United States Patent
Al-Murrani et al.

(10) Patent No.: US 10,704,102 B2
(45) Date of Patent: Jul. 7, 2020

(54) COMPOSITIONS AND METHODS FOR DIAGNOSING AND MONITORING HYPERTHYROIDISM IN A FELINE

(71) Applicant: Hill's Pet Nutrition, Inc., Topeka, KS (US)

(72) Inventors: Samer Waleed Khedheyer Al-Murrani, Topeka, KS (US); Xiangming Gao, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 5 days.

(21) Appl. No.: 16/184,396

(22) Filed: Nov. 8, 2018

(65) Prior Publication Data

US 2019/0071728 A1    Mar. 7, 2019

Related U.S. Application Data

(62) Division of application No. 14/125,981, filed as application No. PCT/US2012/042534 on Jun. 14, 2012, now Pat. No. 10,144,969.

(60) Provisional application No. 61/497,264, filed on Jun. 15, 2011.

(51) Int. Cl.
| | | |
|---|---|---|
| C07H 21/04 | (2006.01) | |
| C12Q 1/68 | (2018.01) | |
| C12Q 1/6883 | (2018.01) | |
| A23L 33/00 | (2016.01) | |
| G01N 33/68 | (2006.01) | |

(52) U.S. Cl.
CPC ............ *C12Q 1/6883* (2013.01); *A23L 33/30* (2016.08); *G01N 33/6893* (2013.01); *A23V 2002/00* (2013.01); *C12Q 2600/158* (2013.01); *G01N 2800/046* (2013.01); *G01N 2800/50* (2013.01)

(58) Field of Classification Search
None
See application file for complete search history.

(56) References Cited

U.S. PATENT DOCUMENTS

| | | |
|---|---|---|
| 4,437,975 A | 3/1984 | Gillespie et al. |
| 4,683,195 A | 7/1987 | Mullis et al. |
| 4,683,202 A | 7/1987 | Mullis |
| 4,800,159 A | 1/1989 | Mullis |
| 4,965,188 A | 10/1990 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,333,675 A | 8/1994 | Mullis et al. |
| 5,409,818 A | 4/1995 | Davey et al. |
| 5,413,909 A | 5/1995 | Bassam et al. |
| 5,445,934 A | 8/1995 | Fodor et al. |
| 5,494,810 A | 2/1996 | Barany et al. |
| 5,541,061 A | 7/1996 | Fodor et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,677,195 A | 10/1997 | Winkler et al. |
| 5,744,305 A | 4/1998 | Fodor et al. |
| 5,770,722 A | 6/1998 | Lockhart et al. |
| 5,800,992 A | 9/1998 | Fodor et al. |
| 5,834,758 A | 11/1998 | Trulson et al. |
| 5,856,092 A | 1/1999 | Dale et al. |
| 5,858,659 A | 1/1999 | Sapolsky et al. |
| 5,861,245 A | 1/1999 | McClelland et al. |
| 5,871,928 A | 2/1999 | Fodor et al. |
| 5,874,219 A | 2/1999 | Rava et al. |
| 5,902,723 A | 5/1999 | Dower et al. |
| 5,936,324 A | 8/1999 | Montagu |
| 5,981,956 A | 11/1999 | Stern |
| 6,013,449 A | 1/2000 | Hacia et al. |
| 6,020,135 A | 2/2000 | Levine et al. |
| 6,025,601 A | 2/2000 | Trulson et al. |
| 6,033,860 A | 3/2000 | Lockhart et al. |
| 6,040,138 A | 3/2000 | Lockhart et al. |
| 6,040,193 A | 3/2000 | Winkler et al. |
| 6,045,996 A | 4/2000 | Cronin et al. |
| 6,063,603 A | 5/2000 | Davey et al. |

(Continued)

FOREIGN PATENT DOCUMENTS

| | | |
|---|---|---|
| CN | 101416685 | 4/2009 |
| WO | WO 88/10315 | 12/1988 |
| WO | WO 9006995 | 6/1990 |
| WO | WO 99/47964 | 9/1999 |
| WO | WO 2008/137549 | 11/2008 |

OTHER PUBLICATIONS

Uyttersprot (Molecular and Cellular Endocrinology, vol. 131, pp. 195-203, 1997) (Year: 1997).*
Effraimidis (European J. of Endocrinology, vol. 164, pp. 107-113, Jan. 2011) (Year: 2011).*
Lecuyer et al. (Can Vet J. vol. 47, pp. 131-135, 2006).
Nann et al (Veterinary Surgery, vol. 35, pates 287-293, 2006).
Affymetrix U133 Plus 2 GeneChip (Affymetrix, 2007).
Merendez et al. ("Gene Expression analysis of feline Thyroid tissue and blood from cats with evidence of mild or marked hyperthyroidism reveals potential molecular causes of the disease and identifies future routes for intervention", Conference Proceedings, 2001).

(Continued)

*Primary Examiner* — Jeanine A Goldberg

(57) ABSTRACT

The present invention provides a method of diagnosing the existence or risk of hyperthyroidism in a feline comprising measuring the level of expression of one or more biomarkers selected from the group consisting of, e.g., IYD, TG, SLC5A5, NIS, TPO, TSHR, DUOX1, DUOX2 (ThOX), TGFB1, CSTD, DCN and SEPP1 and the expression products thereof, in a biological sample from the feline, wherein elevated expression of the one or more biomarkers in the sample relative to a control value for expression in a sample from a normal feline or feline population, or a baseline value from the feline, indicates the existence or risk of hyperthyroidism; a method of treating a feline so diagnosed; and compositions, reagents and kits for carrying out the specified methods.

20 Claims, No Drawings

(56) References Cited

U.S. PATENT DOCUMENTS

| | | | |
|---|---|---|---|
| 6,090,555 A | 7/2000 | Fiekowsky et al. | |
| 6,141,096 A | 10/2000 | Stern et al. | |
| 6,156,501 A | 12/2000 | McGall et al. | |
| 6,177,248 B1 | 1/2001 | Oliner et al. | |
| 6,185,030 B1 | 2/2001 | Overbeck | |
| 6,197,506 B1 | 3/2001 | Fodor et al. | |
| 6,201,639 B1 | 3/2001 | Overbeck | |
| 6,218,803 B1 | 4/2001 | Montagu et al. | |
| 6,225,625 B1 | 5/2001 | Pirrung et al. | |
| 6,284,460 B1 | 9/2001 | Fodor et al. | |
| 6,300,063 B1 | 10/2001 | Lipshutz et al. | |
| 6,300,070 B1 | 10/2001 | Boles et al. | |
| 6,309,822 B1 | 10/2001 | Fodor et al. | |
| 6,333,179 B1 | 12/2001 | Matsuzaki et al. | |
| 6,344,316 B1 | 2/2002 | Lockhart et al. | |
| 6,361,947 B1 | 3/2002 | Dong et al. | |
| 6,368,799 B1 | 4/2002 | Chee | |
| 6,386,749 B1 | 5/2002 | Watts et al. | |
| 6,391,592 B1 | 5/2002 | Su et al. | |
| 6,391,623 B1 | 5/2002 | Besemer et al. | |
| 6,410,276 B1 | 6/2002 | Burg et al. | |
| 6,582,938 B1 | 6/2003 | Su et al. | |
| 6,632,611 B2 | 10/2003 | Su et al. | |
| 6,872,529 B2 | 3/2005 | Su | |
| 6,958,225 B2 | 10/2005 | Dong | |
| 7,689,022 B2 | 3/2010 | Weiner et al. | |
| 2007/0065816 A1 | 3/2007 | Dong | |
| 2009/0226540 A1 | 9/2009 | Wedekind et al. | |

OTHER PUBLICATIONS

Krause et al. (Eur. J. of Endocrinology, vol. 156, pp. 295-301, 2007).
Hebrant et at, "Thyroid Gene Expression in Familial Nonautoimmune Hyperthyroidism Shows common Characteristics with Hyperfunctioning Autonomous Adenomas," J Clin Endocrinol Metab., Jul. 2009, 94(7):2602-2609.
Hoffmann, "Transdermal methimazole treatment in cats with hyperthyroidism," J Feline Med Surg. Apr. 2003; 5(2): 77-82.
Kumar et al., "Evidence for Enhanced Adipogenesis in the Orbits of Patients with Graves'Ophthalmaopathy," J Clin Endocrinol Metab., Feb. 2004. 89(2):930-935.
Turrel et at, "Radioactive iodine therapy in eats with hyperthyroidism," J. Am. Vet. Med. Assoc. Mar. 1, 1984; 184(5): 554-9.
AAFCO; American Feed Control Officials, Inc., Official Publication, pp. 126-140 (2003).
AAFCO; American Feed Control Officials, Inc., Official Publication, pp. 129-137 (2004).
AAFCO; American Feed Control Officials, Inc., Official Publication, pp. 220 (2003).
Altschul et al., "Gapped BLAST and PSI-BLAST: a new generation of protein database search programs," Nucl. Acids Res., 1997, 25:3389-3402.
Ames et al; "The Free Radical Theory of Aging Matures"; Physiol Rev. 78(2):547-581; 1998.
Ames, "A Role for supplements in optimizing health:the metabolic tune-up," Archives of Biochem. and Biophysics, 2004, 423:227-234
Amudha et al; "Protective Effect of Lipoic Acid on Oxidative and Peroxidative Damage in Cyclosporine A-induced Renal Toxicity"; International Immunopharmacology; Nov. 2007; vol. 7, No. 11; pp. 1442-1449; Abstract
Anonymous, "Feline solute carrier family 5 (sodium iodide symporter), member 5," Archive Ensembl release 62, Apr. 2011, Retrieved from http://apr2011.archive.ensemble.org/Feliss_catus/transcript.
Anonymous "Ami Products—Ingredients"; Internet Citation (Online), 2004; Retrieved from the Internet: http://ami.aminews.net/en_ingredienti.html.
Arata et al., "Urinary transforming growth factor-β1 in feline chronic renal failure," J. Vet. Med. Sci., 2005, 67(12)11253-1255.
Arrivazhagan et al; "Effect of dl-alpha Lipoic Acid on Glutathione Metabolic Enzymes in Aged Rats"; Exp. Gerontol. 37:81-87; 2001.
Arrivazhagen et al; "Effect of dl-alpha Lipoic Acid on the Status of Lipid Peroxidation and Antioxidant Enzymes in Various Brain Regions of Aged Rats"; Exp. Gerontol. 37:803; 2002.
Baker. et al:, "Comparative Nutrition of Cats and Dogs"; Amu. Rev, Nutr. 11:239-63; 1991.
Barringer et al., "Blunt-end and single-strand ligations by *Escherichia culi* ligase:influence on an in vitro amplification," Gene, 89:117, 1990.
Ben-Eliiyahu et al; "Evidence that Stress and Surgical Interventions Promote Tumor Development by Suppressing Natural Killer Cell Activity"; Int J Cancer 80:880-888; 1999.
Berkson; "A Conservative Triple Antioxidant Approach to the Treatment of Hepatitis C. Combination of Alpha Lipoic Acid (Thictic Acid), Silymarin, and Selenium: Three Case Histories"; Abstract; Medizinische Klinik; Oct. 1999; vol. 94, Suppl 3, pp. 84-89.
Bezlepkin et al; "The Prolongation fo Survival in Mice by Dietary Antioxidants Depends on Their Age by the Start of Feeding This Diet": Mech Aging Dev; 1999; 92;227-234.
Release of Nrf2 from INrf22 But Not Required for Nrf2 Stabilization/Accumulation in the Nucleas and Transcriptional Activation of ARE-mediated NQO1 Gene Expression; J. Biol. Chem; 2003, 278;44675.
Borras, et al; "Age-related Changes in the Brain of the Dog"; Vet Pathol 36:202-211; 1999.
Brigelius-Flohe, et al; "Vitamin E: Function and Metabolism"; FASEB J 13:1145-1155; 1999.
Cagen et al; "Evaluation of Hepatic Storage of Sulfobromophthalein in Rats and Dogs"; Toxicology 35(4):261-270; 1982.
Cao et al; "Increases in Human Plasma Antioxidant Capacity After Consumption of Controlled Diets High in Fruit and Vegetables"; AM J Clin Nut 68:1081-1087; 1998.
Caprioli. et al., "Age-Dependent deficites in radial maze perfomance in the rat: effect of chronic treatment with acetyl-1-carnitine," Prog. Neuro-Psychopharmacol. & Biol. Psychiat., 1990, 14:359-369 (CA 113:71127).
U.S. Appl. No. 09/916,135, filed Jul. 25, 2001.
Cotman et al; "Brain Aging in the Canine: A Diet Enriched in Antioxidants Reduces Cognitive Dysfunction"; Neurobiology of Aging; 23(5); 809-818; 2002.
Cotten et al., "Ribozyme mediated destruction of RNA in vivo,"EMBO Journal 8(12):3861-3866; 1989.
Davis et al; "Hepatic Glutathione Depletion and Impaired Bromosulphothalein Clearance After Paracetamol Overdose in Man and the Rat", Clinical Science and Molecular Med., 1975, 49(5):495-502.
Dodd et al; Can a Fortified Food Affect Behavioral Manifestations of Age-related Cognitive Decline in Dogs?; Veterinary Medicine; 98; 396-408; 2003.
Dong et al:, "Flexible use of high-density oligonucleotide arrays for single-nucleotide polymorphism discovery and validation" Genome Research, 2001, 11;1418.
Droge; "Oxidative Stress and Aging"; Adv Exp Med Biol; 2003; 543:191-200.
Dru et al; "Evidence-based Management of Feline Lower Urinary Tract Disease"; The Veterinary Clinics of North America, Small Animal Practice; May 2007; vol. 37, No. 3, pp. 533-558.
Eckert et al., "DNA polymerase fidelity and the polymerase chain reaction," PCR Methods and Applications, 1991, p. 17.
Fernandes et al; "Influence of Diet on Survival of Mice"; Proc Natl Acad Sci USA; 1976; 73:1279-1281.
Friesleben et al: "Influence of Selegiline and Lipoic Acid on the Life Expectancy of Immunosuppressed Mice"; Arzneimittelforschung, 1997; 47:776-780.
Fujimoto et al; "The Effect of Dietary Doeosahexaenoate on the Learning Ability of Rats", Health Effects of Fish and Fish Oils; 1989, pp. 275-284.
Gaster; "Antioxidants for Dementia: the Case for Vitamin E"; Alternative Medicine Alert; Feb. 1999.
Gibson, "Antisense approaches to the gene therapy of cancer—'Recnac'," Cancer and Metastasis Reviews 15; 287-299; 1996.
Good et al., "Expression of small, therapeutic RNAs in human cell nuclei,"Gene Therapy; 1997; 4:45-54.

(56) References Cited

OTHER PUBLICATIONS

Grassi et al., "Ribozymes: Structure, Function and Potential Therapy for Dominant Genetic Disorders," Annals of Medicine, 1996, 28:499-510.
Greco; "Dietary Considerations for Dogs with Chronic Renal Failure"; Companion Animal Practice; 1987; vol. 1. No. 1; pp. 54-64.
Guatelli et al., "Isothermal in vitro amplification of nucleic acids by a multienzyme reaction modeled after retroviral replication," Proc. Nat. Acad. Sci. USA, 1990, 87:1874.
Hagen et al; "R-alpha-lipoic Acid Reverses the Age-Associated Increase in Susceptibility of Hepaincytes to Test Butylhydroperoxide Both in Vitro and in Vivo"; Antioxid Redox Signal 20(3):473-483; 2000.
Hall et al., "Dietary antioxidants and behavioral enrichment enhance neutrophil phagocytosis in geriatric beagles," Vet Immunol Immunopathol; 2006, 113(1-2):224-233.
Harman; "Free Radical Theory of Aging: A Hypothesis on Pathogensis of Senile Demential of the Alzheimer's Type"; Age; vol. 16; 23-30; 1993.
Harman; "Prolongation of the Normal Lifespan and Inhibition of Spontaneous Cancer by Antioxidants"; J Gerontol; 1961, 16:247-254.
Hartmann et al., "The Potent free raical scavenger a-Lipoic acid improves memory in aged mice: putative relationship to NMDA receptor deficits," Pharmacology Biochemistry and Behavior, 1993, 46:799-805 (CA 120:45784).
Hayes et al.; "Comparative Cytopathoiogy of Primary Rat Hepatoeyte Cultures Exposed to Aflatoxic B1, Acetaminophen and Other Hepatotoxins"; Toxicol Appl Pharmacol, 80(2):345-356; 1985.
Hayes et al; "The Glunathione S-transferase Supergene Family: Regulation of GST and the Contribution of the Isoenzymes to Cancer Chemoproteetion and Drug Resistance"; Crit Rev Biochem Mel Biol., 1995, 30(6):445-600.
Head et al; "Spatial Learning and Memory as Function of Age in the Dog"; Behavioral Neuroscience 109:851-858; 1995.
Howitz et al; "Small Molecule Activators of Sirtuins Extend *Saccharomyces cereviiae* Lifespan" ; Nature; 2003; 425(6954):191-196.
International Search Report and Written Opinion for PCT/US20122/042534 dated Oct. 25, 2012.
International Search Report of the International Searching Authority dated Dec. 1, 2009 for International Application No. PCT/US2009/051114.
International Search Report of the International Searching Authority dated Nov. 12, 2010 for International Application No. PCT/US2009/069686.
Jha et al., "Dietary (n-3) fatty acids alter plasma fatty acids and leukotriene B synthesis by stimulated neutrophils from healthy geriatric Beagles," Prostaglandins, Leukotrienes, Essential Fatty Acids, Nov. 2005 73(5): 335-341.
Jones et al; "Evidence of the Involvement or Docosahexaenoic Acid in Cholingeric Stimulated Signal Transduction at the Synapse"; Neurochemical Research; 1997; 22:663-670.
Karlin et al., "Methods for assessing the statistical significance of molecular sequence features by using general scoring schemes," Proc. Natl. Acad. Sci, USA, 1990, 87:2264-2268.
Kelly; "Nutritional and Botanical Interventions to Assist With the Adaptation to Stress"; Altern Med Rev 4(4):249-265; 1999.
Khedun et al; "The Effect of Therapeutic Doses of Paracetamol on Liver Function in the Rat Perfused Liver"; J Pharm Pharmacol 45(6);566-569; 1993.
Krause et al., "Characterisation of DEHAL1 expression in thyroid pathologies," European J. of Endocrinology, 2007, 156:295-301.
Kwoh et al., "Transcription-based amplification system and detection of amplified human immunodeficiency virus type 1 with a bead-based sandwich hybridization format," Proc. Natl. Acad. Sci. USA, 1989, 86:1173.
Lamale et al; "Interleukin-6 Histamine, and Methylhistamine as Diagnostic Markers for Interstitial Cystitis"; Urology; vol. 68, No. 4; Oct. 2006: pp. 702-706.
Landegrem et al., "A ligase-mediated gene detection technique," Science, 1988, 241:1077.
Lauterberg et al; "Biliary Excretion of Glutathione and Glutathione Disulfide in the Rat: Regulation and Response to Oxidative Stress"; J Clin Invest 3(1);124-133; 1984.
Leibestseder.; "Effect of Medium Protein Diets in Dogs with Chronic Renal Failure"; J Nutr; 1991; 121(11 Suppl):S145-9.
Leveque; "Cognitive Dysfunction in Dogs, Cat and Alzheimer's-like Disease"; J Am Vet Med Assoc 212:1351; 1998.
Lexis et al; "Alpha-tocopherol and Alpha-Lipoic Acid Enhance the Erythrocyte Antioxidant Defence in Cyclosporine A-treated Rats"; Basic & Clinical Pharmacology & Toxicology; vol. 98; No. 1; Jan. 2006; pp. 68-73.
Loftin et al; "Therapy and Outcome of Suspected Alpha Lipoic Acid Toxicity in Two Dogs"; Journal of Veterinary Emergency and Critical Care; Oct. 2009; vol. 19, No, 5; pp. 501-506.
Logham; "Role of Phosphate Retention in the Progression of Renal Failure"; Lab Clin Med 1993; 122(1):16-26; Abstract.
Lu et al., "In vivo application of RNA interference: from functional genomics to therapeutics," Advances in Genetics, 2005, 54:117-42
Ma et al; "Inhibition of Nuclear Factor KappaB by Phenolic Antioxidants: Interplay Between Antioxidant Signaling and Inflammatory Cytokine Expression"; Mol Pharmacal 64(2);211-210; 2003.
Mantovani et al; "Antioxidant Agents are Effective in inducing Lymphocyte Progression Through Cell Cycle in Advanced Cancer Patients; Assessment of the Most Important Laboratory Indexes of Cachexia and Oxidative Stress"; J Mol Med 81(10):664-673, 2003.
Massie et al; "Effect of Dietary Beta-Carotene on the Survival of Young and Old Mice"; J Gerontol; 1986; 32;189-195.
Matsuhiro et al., "Molecular cloning and functional expression of feline thrombopoietin," Vet. Immunology and Immunopathology. 1998, 66:225-236.
Mattila et al., "Fidelity of DNA synthesis by the Thermocoecus litoralis DNA polymerase-an extremely heat stable enzyme with proofreading activity," Nucleic Acids Res, 19, 1991, 4967.
Mattina; "Analysis of Agricultural Feeds and Pet Foods 1998"; Connecticut Agricultural Experiment Station; 1998.
McCloskey et al; "Resistance of Three Immortalized Human Hepatocyte Cell Lines to Acetaminophen and N-acetyl-p-benoquinoneimine Toxicity"; J Hepatol 31:841-851; 1999.
McGahon et al; "Age-related Changes in Oxidative Mechanisms and LTP are Reversed by Dietary Manipulation"; Neurobiology of Aging 1999; 20:643-653.
McGahon et al; "Age-related Changes in Synaptic Function: Analysis of the Effect of Dietary Supplementation with Omega-3 Fatty Acids"; Neuroscience; 1999; 94:305-314.
Evidence of Mild or Marked Hyperthyroidism Reveals Potential Molecular Causes of the Disease and Identifies Future Routes for Intervention, Research Abstract Program 2011 ACVIM Forum, Retrieved from http://onlinelibrary.wiley.com/doi/10.1111/j.1939-1676.2011.0726,x/abstract, May.
Michal et al., "Modulatory effects of dietary beta-carotene on blood and mammal, leukocyte function in periparturient dairy cows," J. Dairy Sci,; 1994: 77:1408-1421.
Michaud et al, (2002) Proteomic approaches for the global analysis of proteins. Biotechniques 33, 1308-1316.
Michel; "Interventional Nutrition for the Critical Care Patient: Optimal Diets"; Clinical Techniques in Small Animal Practice; 1998: 13(4):204-210.
Milgram et al; "Cognitive Functions and Aging in the Dog: Acquisition of Nonspatial Visual Tasks"; Behavioural Neuroscience 108:57-68; 1994.
Milgram et al; "Landmark Discrimination Learning in the Dog"; Learning & Memory: 6:54-61; 1999.
Milgram et al; "Long-term Treatment with Antioxidants and a Program of Behavioral Enrichment Reduces Age-Dependent Impairment in Discrimination and Reversal Learning in Beagle Dogs"; Exp Gerontol; 2004; 39:753-765.
Milgram et al; Internet Web site; "Landmark Discrimination Learning in Aged Dogs is Improved by Treatment with an Antioxidant Enriched Diet"; Oct. 2000.

(56) References Cited

OTHER PUBLICATIONS

Miller et al., "RNA interference in neuroscience: progress and challenges," Cellular and Molecular Neurobiology, 25:1195-207 (2005).
Minazaki et al., "Acid phosphatase and cathepsin D are active expressed enzymes in the placenta of the cat," Research in Veterinary Science, 2008, 84:326-334.
Mitchell et al; "Role of Glutathione in the Cytotoxicity of Acetaminophen in a Primary Culture System of Rat Hepatocytes"; Toxicology, 1985 37:127-146.
Nastevska et al.; "Impairment of TNF-alpha Expression and Secretion in Primary Rat Liver Cell Cultures by Acetaminophen Treatment"; Toxicology 13(2-3):85-92; 1999.
National Research Council; Nutrient Requirements of Dogs and Cats; Nat'l Academy Press, Washington, DC; 2006: pp. 359-360.
Nielson, "Applications of peptide nucleic acids," Curr. Opin. Biotechnol., 1999, 10:71-75.
Nguyen et al., "Cloning of the Cat TSH Receptor and Evidence Against an Autoimmune Etiology or Feline Hyperthyroidism," Endocrinology, Jan. 2002, 143(2):395-402.
Nielson et al., "Sequence-selective recognition of DNA by strand displacement with a thymine-substituted polyamide," Science, 1991, 254:1497-1500.
Otto et al; "Glutathione Regulates 3,3',44'-tetrachlorobiphenyl Induced Cytochrome P450 Metabolism: Evidence for a Cross-talk Between the Major Detoxification Pathways"; Biochem Mol Biol Int 38(6):1127-1133; 1996.
Otto et al; "Regulation of Cytochrome P4501A Metabolism by Glutathione"; Pharmacol Toxicol 84(5):201-210; 1999.
Patrick; "Nutrients and HIV: Part Three—N-Acetylcysteine, Alpha-Lipoic Acid, L-Glutamine, and L-Carnitine"; Alternative Medicine Review; vol. 5, No, 4; 2000; pp. 290-305.
Polzin et al "Dietary Management of Feline Chronic Renal Failure: Where are We Now? In What Direction are We Headed?"; Journal of Feline Medicine and Surgery; 2000; pp. 75-82 XP002446902 ISSN: 1098-612X.
Rayment et al; "Vitamin C Supplementation in Normal Subjects Reduces Constitutive ICAM-1 Expression"; Biochem Biophys Res Commun 308(2):339-345; 2003.
Rimbach et al., "Regulation of cell signaling by vitamin E," Proceedings of the Nutrition Society; 2002; 61;415-425.
Rosler et al; "Free Radicals in Alzheimer's Dementia: Currently Available Therapeutic Strategies"; J Neural Transm Suppl; 1998; pp. 211-219.
Rudick et al; "Mast Cell-Derived Histamine Mediates Cystitis Pain"; Journal of Urology; vol. 179, No, 4, p. 62; Apr. 2008.
Ruehl, "Anipryl: Hope of Controlling Canine Cognitive Dysfunction Syndrome"; Topics in Veterinary Medicine; 1999.
Sano et al; "A Controlled Trial of Selegiline, Alpha-Tocopherol, or Both as Treatment for Alzheimer's Disease"; The New England Journal of Medicine; vol, 336, 1997; pp. 1216-1222.
Schmidt et al; "Effect of Dietary Lipoic Acid on Metabolic Hormones and Acute-Phase Proteins During Challenge with Infectious Bovine Rhinotracheitis Virus in Cattle"; Am J Vet Res; Jul. 2006; 67(7): 1192-8.
Shoulson; "Deprenyl and Toeopherol Antioxidinive Therapy of Parkinsonism (DATATOP). Parkinson Study Group"; Acta Neural Scand Suppl: 1989; 126:171-5.
Siwak et al; "Locomotor Activity in Dogs Vary with Age and Cognitive Status"; Behavioral Neuroscience, 117: 813-824; 2003.
Snel et al; "Glutathione Conjugation of Bromosulfophthalein in Relation to Hepatic Glutathione Content in the Rat in Vivo and in the Perfused Rat Liver"; Hepatology, 1995, 21(5):1387-1394.
Snel et al; "Methods for the Quantitation of Bromosulfophthalein and its Glutathione Conjugate in Biological Fluids"; Anal Biochem 212(1):28-34; 1993.
St. Omer et al; "Effect of Antidotal N-acetylcysteine on the Pharmacokinetics of Acetaminophen in Dogs": J. Vet. Pharmacol, Therap., 1984, 7:277-281.
Turturro et al; "Dietary Alteration in the Rates of Cancer and Aging"; Exp Gerontol, 1992, 27:583-592.
Vatassery et al; "High Doses of Vitamin F in the Treatment of Disorders of the Central Nervous System in the Aged"; Am J Clin Nutr; 1999; 70:793-801.
Vendemiale et al; "Effect of Acetaminophen Administration on Hepatic Glutathione Compartmentation and Mitochondrial Energy Metabolism in the Rat"; Biochem Pharmacol 52(8); 1147-1154; 1996.
Wallace et al.; "s-Adenosyl-L-methionine (SAMe) for the Treatment of Acetominophen Toxicity in a Dog"; J Am Anim Hosp Assoc, 2002, 38(3):246-2544.
Ward et al., "Thyrotropim-stimulated DNA synthesis and thyroglobulin exptession in normal and hyperthyroid feline thyrocytes in monolayer culture," Thyroid, 2005, 15(2):114-120.
Weaver et al.; "Health Effects and Metabolism of Dietary Eicosapentaenoic Acid"; Pro Food Nutr Sci; 1998; 12:111-150.
Wu et al., "The ligation amplification reaction (LAR)—amplification of specific DNA sequences using sequential rounds of template-dependent ligation," Genomics, 1989, 4:560.
Yasuda et al; "Mechanism of Protection by S-(1,2-dicarboxyethyl)glutathione Triester Against Acetaminophen-induced Hepatotoxicity in Rat Hepatocytes": Biol Pharm Bull 24(7):749-753, 2001.
Youdim et al.; "Essential Fairy Acids and the Brain: Possible Health Implications", Int J Devl Neurosciences; 2000; 18:383-399.
Young et al.; "Efficient isolation of genes by using antibody probes," P.N.A.S. 1983, 80: 1194.
Zhou et al.; "Localization of Glutathione Conjugation Activites Toward Bromosulfophthalein in Perfused Rat Liver: Studies with the Multiple Indicator Dilution Technique"; Drug Metab Dispo; 21(6), 1070-1078; 1993.
Zhou et al.; "Selective Mitochondrial Glutathione Depletion by Ethanol Enhances Acetaminophen Toxicity in Rat Liver"; Hepatology, 2002, 36(2):326-325.

* cited by examiner

COMPOSITIONS AND METHODS FOR DIAGNOSING AND MONITORING HYPERTHYROIDISM IN A FELINE

CROSS-REFERENCE TO RELATED PATENT APPLICATIONS

This application is a divisional application of U.S. patent application Ser. No. 14/125,981, filed on Nov. 25, 2014, which is a national stage entry under 35 U.S.C. § 371 of International Patent Application No. PCT/US2012/042534, filed 14 Jun. 2012, which claims priority to U.S. Provisional Patent Application Ser. No. 61/497,264, filed on 15 Jun. 2011, both of which are incorporated herein by reference.

FIELD OF THE INVENTION

The present invention relates to compositions, materials and methods for diagnosing and/or monitoring hyperthyroidism in felines and diseases and disorders in felines relating to or resulting from hyperthyroidism.

BACKGROUND OF THE INVENTION

Hyperthyroidism is the most common hormone abnormality in felines. It is most common in older felines, and somewhat more common in females than in males. Hyperthyroidism is caused by overproduction of thyroid hormones, particularly thyroxine or T-4. Overproduction of T-4 can dramatically increase the animal's basal metabolic rate, leading to weight loss, increased appetite, restlessness, poor hair coat, tachycardia, increased drinking and urination, vomiting, diarrhea, panting, difficulty breathing, fever, elevated blood pressure, and eventually weakness, listlessness, muscle tremors, wasting, and death. Advanced hyperthyroidism is often associated with kidney problems and heart problems. Effective treatments include use of drugs such as methimazole or carbimazole, which inhibit production of thyroid hormones, radioiodine therapy, which destroys overactive thyroid cells, and surgical thyroidectomy. If the disease is detected too late, however, the damage may be irreversible. Accordingly, early diagnosis is critical.

The most common test for diagnosing hyperthyroidism is a blood test for T-4, where significantly elevated T-4 levels indicate hyperthyroidism, or a T-3 suppression test, which measures suppression of T-4 in response to administration of T-3, wherein absence of suppression indicate a hyperthyroid condition. However, a feline's level of T-3 and T-4 may fluctuate in the course of the day, rendering tests unreliable, and there are also various diseases that can artificially lower T-4 levels, thus masking a hyperthyroid condition. Radioimaging of the thyroid using technetium is possible, and may be useful to detect tumors or abnormal thyroid tissues, but it is expensive.

Accordingly, there is a need for alternative efficient and effective methods of detecting hyperthyroidism in felines.

A number of methods have been developed for studying differential gene expression, e.g., DNA microarrays, expressed tag sequencing (EST), serial analysis of gene expression (SAGE), subtractive hybridization, subtractive cloning and differential display (DD) for mRNA, RNA-arbitrarily primed PCR (RAP-PCR), real-time PCR (RT-PCR), representational difference analysis (RDA), two-dimensional gel electrophoresis, mass spectrometry, and protein microarray based antibody-binding for proteins.

Due to the complexity of the biological pathways implicated in hyperthyroidism and the inherent molecular interactions and intercellular signaling processes, it is highly desirable to understand at a genetic level the interactions that are taking place. Detection of dysregulated genes in the early stages of hyperthyroidism in felines is helpful in understanding the biology of hyperthyroidism in felines on a genome-wide basis, which would be helpful in designing methods for determining the risk of developing, predisposition for, diagnosing of, and devising and monitoring a treatment plan for hyperthyroidism.

A more detailed understanding of the biological pathways involved through gene expression profiling would aid in the development of diagnostic procedures, reagents and test kits as well as salutary pharmaceutical, nutraceutical and nutritional (dietary) interventions in the disease pathways. These approaches may enable early detection and potentially prevention or treatment of the underlying disorder. Dysregulated genes involved in the pathology of thyroid disorders may serve as important biomarkers for diagnosis and potentially prevention or treatment of the disorder and to optimize selection of appropriate pharmaceutical, nutraceutical and nutritional (dietary) interventions.

The level of gene expression and/or the determination of the level of functioning of an expressed gene product in a feline may be used to select an appropriate agent for therapeutic or prophylactic use. This data may be employed by the skilled worker in selecting appropriate drugs as agents for the prevention or treatment of renal diseases in felines through gene expression profiling. Gene expression data and analysis may also be used to select nutritional compositions, dietary supplements, and nutraceuticals having a salutary effect on promoting normal thyroid function performance by utilizing biomarkers indicative of a healthy state of kidney functioning.

Only very limited work has been done to date in screening the feline genome for gene expression profiles in connection with the diagnosis of diseases in felines. Studies in healthy populations of felines versus populations having a disease such as hyperthyroidism as described in this specification have not been extensively conducted. Little data is available with respect to the expression profile of the feline genome, especially with respect to the development of renal diseases in felines over time.

Hyperthyroidism is a leading cause of death in felines. To effectively treat hyperthyroidism, early diagnosis and treatment is essential, before there is irreversible damage to the heart and/or kidneys. Accordingly, there is a need for better methods to identify animals having hyperthyroidism or at elevated risk for hyperthyroidism, so that they can be treated appropriately.

SUMMARY OF THE INVENTION

The inventors have studied gene expression in thyroid tissue and whole blood in felines with hyperthyroidism. In the tissue study, 1308 significant differential expression genes are found between hyperthyroid felines and non-hyperthyroid felines with FDR (False discovery rate)=0.1 and fold change of >=+/−1.25 in expression. In the whole blood study, 1094 significant genes are found between hyperthyroid felines and non-hyperthyroid felines with the same cutoff as shown above. In the tissue study, all the genes known to be involved in the pathway leading to the production of thyroid hormones are found to be up-regulated in the hyperthyroid felines. The increased expression of these genes clearly contributes to a high T4 production in the feline body. In the whole blood study, 60 genes are found to overlap with those found from the solid tissue work that appear to be regulated in the same direction as seen in the tissue study. By using these 60 genes, the hyperthyroid felines can be distinguished from the normal felines as tested in the whole blood, as well as in the tissue. These 60 genes, listed in Tables A and B below, may permit detection of feline hyperthyroidism.

Accordingly, the present invention provides compositions, materials and methods for diagnosing and/or monitoring hyperthyroidism in felines and diseases and disorders in felines relating to or resulting from hyperthyroidism, including compositions and methods for: determining the risk of developing, identifying a predisposition for, diagnosing of, devising and monitoring a treatment plan for, and monitoring the status of hyperthyroidism in a feline, wherein the hyperthyroidism is detectable by utilizing at least one relevant biomarker isolated and measured from a biological test sample taken from such feline, wherein the expression of the biomarker correlates positively or negatively with the disease. A relevant biomarker for practice of the compositions and methods of the present invention comprises a polynucleotide or protein present in such biological test sample of such feline. A biological test sample for the practice of the method of the invention may comprise, for example, a tissue sample from such feline. The biomarkers are selected also on the basis of being secreted, so they can be detected in blood serum or plasma, or in urine. Accordingly the biological test sample may also be a specimen of a biological fluid taken from such feline, for example blood or urine.

Genes which are found to be particularly up-regulated in thyroid hormone overproduction include:

IYD (4.55 fold increase): This gene encodes an enzyme that catalyzes the oxidative NADPH-dependent deiodination of mono- and diiodotyrosine, which are the halogenated byproducts of thyroid hormone production. The N-terminus of the protein functions as a membrane anchor. Mutations in this gene cause congenital hypothyroidism due to dyshormonogenesis type 4, which is also referred to as deiodinase deficiency, or iodotyrosine dehalogenase deficiency, or thyroid hormonogenesis type 4.

TG (2.02 fold increase): Thyroglobulin (Tg) is a glycoprotein homodimer produced predominantly by the thyroid gland. It acts as a substrate for the synthesis of thyroxine and triiodothyronine as well as the storage of the inactive forms of thyroid hormone and iodine. Thyroglobulin is secreted from the endoplasmic reticulum to its site of iodination, and subsequent thyroxine biosynthesis, in the follicular lumen. Mutations in this gene cause thyroid dyshormonogenesis, manifested as goiter, and are associated with moderate to severe congenital hypothyroidism.

SLC5A5, NIS (4.6 fold increase): This gene encodes a member of the sodium glucose cotransporter family. The encoded protein is responsible for the uptake of iodine in tissues such as the thyroid and lactating breast tissue. The iodine taken up by the thyroid is incorporated into the metabolic regulators triiodothyronine (T3) and tetraiodothyronine (T4). Mutations in this gene are associated with thyroid dyshormonogenesis 1.

TPO (4.06 fold increase): This gene encodes a membrane-bound glycoprotein. The encoded protein acts as an enzyme and plays a central role in thyroid gland function. The protein functions in the iodination of tyrosine residues in thyroglobulin and phenoxy-ester formation between pairs of iodinated tyrosines to generate the thyroid hormones, thyroxine and triiodothyronine. Mutations in this gene are associated with several disorders of thyroid hormonogenesis, including congenital hypothyroidism, congenital goiter, and thyroid hormone organification defect IIA.

TSHR (2.2 fold increase): The protein encoded by this gene is a membrane protein and a major controller of thyroid cell metabolism. The encoded protein is a receptor for thyrothropin and thyrostimulin, and its activity is mediated by adenylate cyclase. Defects in this gene are a cause of several types of hyperthyroidism.

DUOX2, ThOX (1.55 fold increase): The protein encoded by this gene is a glycoprotein and a member of the NADPH oxidase family. The synthesis of thyroid hormone is catalyzed by a protein complex located at the apical membrane of thyroid follicular cells. This complex contains an iodide transporter, thyroperoxidase, and a peroxide generating system that includes this encoded protein and DUOX1. This protein is known as dual oxidase because it has both a peroxidase homology domain and a gp91phox domain.

Other genes which are up-regulated in both blood and thyroid tissue of hyperthyroid felines include the following:

TABLE A

| | |
|---|---|
| CHI3L1 | chitinase 3-like 1 (cartilage glycoprotein-39) |
| PDZK1IP1 | PDZK1 interacting protein 1 |
| MAPK13 | mitogen-activated protein kinase 13 |
| PGD | phosphogluconate dehydrogenase |
| MBOAT7 | membrane bound O-acyltransferase domain containing 7 |
| CTSD | felinehepsin D |
| CYP4F3 | cytochrome P450, family 4, subfamily F, polypeptide 3 |
| TGFB1 | transforming growth factor, beta 1 |
| C20orf3 | chromosome 20 open reading frame 3 |
| ACAA2 | acetyl-CoA acyltransferase 2 |
| HTATIP2 | HIV-1 Tat interactive protein 2, 30 kDa |
| RHOC | ras homolog gene family, member C |
| G6PD | glucose-6-phosphate dehydrogenase |
| GSTP1 | glutathione S-transferase pi 1 |
| CAPG | capping protein (actin filament), gelsolin-like |
| AP1S1 | adaptor-related protein complex 1, sigma 1 subunit |
| ATP6V1D | ATPase, H+ transporting, lysosomal 34 kDa, V1 subunit D |
| CAPN1 | calpain 1, (mu/I) large subunit |
| LASS4 | LAG1 homolog, ceramide synthase 4 |
| PDCL | phosducin-like |
| HSD3B7 | hydroxy-delta-5-steroid dehydrogenase, 3 beta- and steroid delta-isomerase 7 |
| LRPAP1 | low density lipoprotein receptor-related protein associated protein 1 |
| PARP3 | poly (ADP-ribose) polymerase family, member 3 |
| ATP6AP1 | ATPase, H+ transporting, lysosomal accessory protein 1 |
| B3GNT8 | UDP-GlcNAc:betaGal beta-1,3-N-acetylglucosaminyltransferase 8 |
| SORT1 | sortilin 1 |

Thus, for example, up-regulation of the genes on this table A can serve as biomarkers for hyperthyroidism. These genes are not previously known to be involved in hyperthyroidism. For example, TGFB1 encodes a member of the transforming growth factor beta (TGFB) family of cytokines, which are multifunctional peptides that regulate proliferation, differentiation, adhesion, migration, and other functions in many cell types. The protein positively and negatively regulates many other growth factors. The secreted protein is cleaved into a latency-associated peptide (LAP) and a mature TGFB1 peptide. The mature peptide may also form heterodimers with other TGFB family members. This gene is frequently up-regulated in tumor cells, and mutations in this gene result in Camurati-Engelmann disease. It is not previously known to be involved in thyroid function. CSTD encodes a lysosomal aspartyl protease. This proteinase, which is a member of the peptidase C1 family, has a specificity similar to but narrower than that of pepsin A. Transcription of this gene is initiated from several sites, including one which is a start site for an estrogen-regulated transcript. Mutations in this gene are involved in the pathogenesis of several diseases, including breast cancer and possibly Alzheimer disease. This gene is not previously known to be involved in thyroid function.

Genes which are down-regulated in both blood and thyroid tissue of hyperthyroid felines include:

TABLE B

| | |
|---|---|
| C13orf27 | chromosome 13 open reading frame 27 |
| GP1BB | glycoprotein Ib (platelet), beta polypeptide |
| IGLL1 | immunoglobulin lambda-like polypeptide 1 |
| LRRC4B | leucine rich repeat containing 4B |
| MALT1 | mucosa associated lymphoid tissue lymphoma translofelineion gene 1 |
| REV3L | REV3-like, felinealytic subunit of DNA polymerase zeta (yeast) |
| GNL3 | guanine nucleotide binding protein-like 3 (nucleolar) |
| RNPC3 | RNA-binding region (RNP1, RRM) containing 3 |
| LMO4 | LIM domain only 4 |
| RFXAP | regulatory factor X-associated protein |
| MPP6 | membrane protein, palmitoylated 6 (MAGUK p55 subfamily member 6) |
| DTWD1 | DTW domain containing 1 |
| MYC | v-myc myelocytomatosis viral oncogene homolog (avian) |
| TCEA3 | transcription elongation factor A (SII), 3 |
| RPAP2 | RNA polymerase II associated protein 2 |
| ZNF292 | zinc finger protein 292 |
| CSGALNACT1 | chondroitin sulfate N-acetylgalactosaminyltransferase 1 |
| ZFP37 | zinc finger protein 37 homolog (mouse) |
| IGJ | immunoglobulin J polypeptide, linker protein for immunoglobulin alpha and mu polypeptides |
| LTBP1 | latent transforming growth factor beta binding protein 1 |
| ABCA5 | ATP-binding cassette, sub-family A (ABC1), member 5 |
| GPRASP2 | G protein-coupled receptor associated sorting protein 2 |
| ARMCX1 | armadillo repeat containing, X-linked 1 |
| SEPP1 | selenoprotein P, plasma, 1 |
| DCN | decorin |

Thus for example, downregulation of the genes on this table B can serve as biomarkers for hyperthyroidism. For example, the protein encoded by the DCN gene is a small cellular or pericellular matrix proteoglycan that is closely related in structure to biglycan protein. It is a component of connective tissue, binds to type I collagen fibrils and plays a role in matrix assembly. It is capable of suppressing the growth of various tumor cell lines. This gene is a candidate gene for Marfan syndrome. It is not previously known to be related to thyroid function. SEPP1 is a secreted protein and is unusual in that it contains 10 selenocysteine residues per polypeptide, constituting most of the selenium in plasma. It has been implicated as an extracellular antioxidant and in the transport of selenium, but is not previously known to be involved in thyroid function.

The invention provides, therefore, a method (Method 1) of diagnosing hyperthyroidism or measuring risk of, or predisposition to, hyperthyroidism in a feline, by measuring the expression level of one or more biomarkers in said feline, said one or more biomarkers selected from the group consisting of the genes listed on Table A (e.g., TGFB1 and/or CSTD) and B (e.g., DCN and/or SEPP1), or any of the following genes: IYD, TG, SLC5A5, NIS, TPO, TSHR, DUOX1 and DUOX2 (ThOX); the expression products of these genes; and any combinations thereof, wherein altered expression of one or more, e.g., at least three, for example five or more, e.g. at least ten, of said biomarkers relative to a normal population or altered expression relative to the feline's individual baseline indicates hyperthyroidism or an increased risk of or predisposition to hyperthyroidism, e.g, according to any of the following methods 1.1. Method 1 wherein the level of expression of the one or more biomarkers is determined using either (i) a DNA microarray comprising one or more oligonucleotides complementary to mRNA or cDNA corresponding to the one or more marker genes to be measured, or (ii) a quantitative polymerase chain reaction with oligonucleotide primers for mRNA or cDNA corresponding to the one or more marker genes to be measured, e.g.
  a. The foregoing method wherein the step of measuring gene expression of one or more biomarkers comprises (i) isolating RNA from the tissue sample, (ii) reverse transcribing the RNA to obtain the corresponding cDNA, (iii) isolating and fragmenting the cDNA thus obtained, (iv) contacting the cDNA fragments with a DNA microarray comprising one or more oligonucleotides complementary to cDNA corresponding to the one or more biomarkers to be measured, and (v) detecting hybridization between the cDNA fragments and the one or more oligonucleotides in the DNA microarray.
  b. Any of the preceding methods involving detecting hybridization wherein the hybridization between the cDNA fragments and the one or more oligonucleotides in the DNA microarray is under stringent conditions.
1.2. Method 1 wherein the level of expression of the biomarker is detected by an antibody to the expressed protein.
  a. Method 1.2 wherein the biomarker is detected by an immunoassay selected from a competitive binding assay, a non-competitive binding assay, a radioimmunoassay, an enzyme linked immunosorbent assay (ELISA), a sandwich assay, a precipitin reaction, a gel diffusion immunodiffusion assay, an agglutination assay, a fluorescent immunoassay, chemiluminescence immunoassay, immunoPCR immunoassay, a protein A or protein G immunoassay and an immunoelectrophoresis assay.
  b. The foregoing method which is an enzyme-linked immunosorbent assay (ELISA).
  c. Method 1.2 wherein the assay is a lateral flow immunochromatographic assay.
  d. Method 1.2 wherein the biological sample is blood or urine.
1.3. Method 1 wherein the level of expression of the biomarker is detected by quantitative mass spectroscopy measuring the expressed protein in the biological sample, e.g., wherein the biological sample is blood or urine.
1.4. Method 1 wherein the level of expression of the biomarker is detected by an aptamer recognizing the expressed protein.
  a. Method 1.4 wherein the aptamer is an oligonucleotide.
  b. Method 1.4 wherein the aptamer is a peptide.
  c. Method 1.4 wherein the biological sample is blood or urine.
1.5. Any of the preceding methods wherein the level of expression of the one or more biomarkers in the biological sample relative to a control value for expression in normal sample is greater than 1.25 fold, e.g., at least 30% change.
1.6. Any of the preceding methods wherein the level of expression of the one or more biomarkers in the biological sample is normalized relative to expression of one or more genes known to have relatively constant expression.
1.7. Any of the preceding methods wherein the biological sample is a sample of thyroid tissue.
1.8. Any of the preceding methods wherein the biological sample is blood.
1.9. Any of the preceding methods further comprising providing to a feline diagnosed with hyperthyroidism, or an increased risk of or predisposition to hyperthyroidism, a diet which is restricted in one or more of iodine, selenium or arachidonic acid, e.g., a diet wherein the level of iodine is less than 0.35 mg/kg, e.g., 0.01-0.25 mg/kg, the level of selenium is less than 0.1 mg/kg, e.g., 0.01-0.05 mg/kg, and/or the level of arachidonic acid is less than or equal to 0.02%, e.g., 0.005-0.01%.
1.10. Any of the preceding methods further comprising administering to a feline diagnosed with hyperthyroidism, or an increased risk of or predisposition to hyperthyroidism, a treatment to reduce thyroid hormone production, e.g., administering an effective amount of a drug which inhibits production of T-4, e.g., methimazole or carbimazole, and/or administering radioiodine therapy, and/or performing a surgical thyroidectomy.

In a further embodiment, the invention provides reagents, optionally labeled, useful in the detection of the level of expression of one or more biomarkers selected from the group consisting of IYD, TG, SLC5A5, NIS, TPO, TSHR, DUOX1, or DUOX2 (ThOX), or from Table A or B, e.g., TGFB1, CSTD, DCN or SEPP1, and the expression products thereof, e.g.,
  a. Antibodies, for example monoclonal antibodies, single chain antibodies, and functional antibody fragments, recognizing feline proteins selected from the group consisting of the expression products of IYD, TG, SLC5A5, NIS, TPO, TSHR, DUOX1, or DUOX2 (ThOX), or genes from Table A or B, e.g., TGFB1, CSTD, DCN or SEPP1.
  b. Aptamers, for example nucleic acid or peptidic aptamers, recognizing feline proteins selected from the group consisting of the expression products of IYD, TG, SLC5A5, NIS, TPO, TSHR, DUOX1, or DUOX2 (ThOX), or genes from Table A or B, e.g., TGFB1, CSTD, DCN or SEPP1.
  c. Isolated and purified or recombinant feline protein selected from the group consisting of the expression products of IYD, TG, SLC5A5, NIS, TPO, TSHR, DUOX1, or DUOX2 (ThOX), or genes from Table A or B, e.g., TGFB1, CSTD, DCN or SEPP1.
  d. Oligonucleotide probes capable of hybridizing to a feline gene selected from the group consisting of IYD, TG, SLC5A5, NIS, TPO, TSHR, DUOX1, or DUOX2 (ThOX), or genes from Table A or B, e.g., TGFB1, CSTD, DCN or SEPP1.
  e. In a further embodiment, the invention provides a kit (Kit 1) for the diagnosis, prognosis or monitoring a thyroid disorder in a feline, comprising
    i. means for measuring gene expression of one or more biomarkers selected from the group consisting of IYD, TG, SLC5A5, NIS, TPO, TSHR, DUOX1, or DUOX2 (ThOX), or from Table A or B, e.g., TGFB1, CSTD, DCN or SEPP1, and the expression products thereof, in a biological sample from the feline, and
    ii. instructions for using such means to measure expression of the one or more biomarkers in a biological sample from the feline and evaluating the risk, predisposition or presence of a process leading to a thyroid disorder in the feline, e.g.
1.1 Kit 1 wherein the means for measuring the one or more biomarkers is one or more nucleic acid probes capable of detecting gene expression of the one or more biomarkers;
1.2 Any of the preceding kits comprising a DNA microarray comprising one or more nucleic acid probes capable of detecting gene expression of the one or more biomarkers.
1.3 Kit 1 wherein the means for measuring the one or more biomarkers is one or more antibodies capable of detecting gene expression of the one or more biomarkers by recognizing the expressed protein.
1.4 Kit 1.3 in ELISA format comprising antibody capable of detecting the one or more biomarkers; isolated, purified or recombinant protein corresponding to the expressed protein; and buffer.
1.5 Kit 1 wherein the means for measuring the one or more biomarkers is one or more aptamers, e.g., as hereinbefore described, capable of detecting gene expression of the one or more biomarkers by recognizing the expressed protein.
1.6 Any of the foregoing kits adapted for use in any of the foregoing Method 1 et seq.

The invention further provides the use of
a nucleotide sequence corresponding to or complementary to a gene for IYD, TG, SLC5A5, NIS, TPO, TSHR, DUOX1, or DUOX2 (ThOX), or from Table A or B, e.g., TGFB1, CSTD, DCN or SEPP1,
or of an antibody to a protein selected from IYD, TG, SLC5A5, NIS, TPO, TSHR, DUOX1, or DUOX2 (ThOX), or from Table A or B, e.g., TGFB1, CSTD, DCN or SEPP1, or
of an aptamer to a protein selected from IYD, TG, SLC5A5, NIS, TPO, TSHR, DUOX1, or DUOX2 (ThOX), or from Table A or B, e.g., TGFB1, CSTD, DCN or SEPP1, or
isolated, purified or recombinant feline protein selected from IYD, TG, SLC5A5, NIS, TPO, TSHR, DUOX1, or DUOX2 (ThOX), or from Table A or B, e.g., TGFB1, CSTD, DCN or SEPP1,
in a method according to Method 1, et seq., or
in the manufacture of a kit according to Kit 1, et seq.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiments is merely exemplary in nature and is in no way intended to limit the invention, its application, or uses.

Certain Definitions

The term "antibody" means any immunoglobulin that binds to a specific antigen, including IgG, IgM, IgA, IgD, and IgE antibodies. The term includes polyclonal, monoclonal, monovalent, humanized, heteroconjugate, antibody compositions with polyepitopic specificity, chimeric, bispecific antibodies, diabodies, single-chain antibodies, and antibody fragments such as Fab, Fab', F(ab')$_2$, and Fv, or other antigen-binding fragments.

The term "array" means an ordered arrangement of at least two probes on a substrate. At least one of the probes is a control or standard and at least one of the probes is a diagnostic probe. The arrangement of from about two to about 40,000 probes on a substrate assures that the size and signal intensity of each labeled complex formed between a probe and a sample polynucleotide or polypeptide is individually distinguishable. The collection of molecules deposited on the array may be prepared either synthetically or biosynthetically. The array may take a variety of forms including libraries of soluble molecules, libraries of compounds tethered to resin beads, silica chips or other solid supports. The nucleic acid array may include libraries of nucleic acids which can be prepared by spotting nucleic acids in essentially any length (for example, from 1 to about 1,000 nucleotides in length) onto a substrate. A nucleic acid probe array preferably comprises nucleic acids bound to a substrate in known locations. In other embodiments, the system may include a solid support or substrate, such as a membrane, filter, microscope slide, microwell, sample tube, bead, bead array, or the like. The solid support may be made of various materials, including paper, cellulose, nylon, polystyrene, polycarbonate, plastics, glass, ceramic, stainless steel, or the like. The solid support may preferably have a rigid or semi-rigid surface, and may preferably be spherical (e.g., bead) or substantially planar (e.g., flat surface) with appropriate wells, raised regions, etched trenches, or the like. The solid support may also include a gel or matrix in which nucleic acids may be embedded.

The term "biomarkers" refers to genes and gene products encoded by a gene of the invention or a homolog thereof, especially a feline homolog thereof, wherein the gene has been determined to have been differentially expressed as a result of a disease, condition, disorder or the administration of a substance, drug, nutrient or dietary component or combinations thereof. A biomarker may be a polynucleotide, polypeptide, protein, RNA, including an RNA transcript or its translation product, DNA, cDNA, a metabolite of one or more of the foregoing molecules, or a useful variant of any one of the foregoing molecules, the differential expression of which is associated with a thyroid disorder, and wherein the correlation of such differential expression in a sample taken from a test animal to a sample taken from a control animal can be used in the diagnosis, prognosis, monitoring or treatment of condition, disease or disorder in an animal in need thereof. In addition, a biomarker can be generally used to refer to any portion or segment of such gene or protein that can identify or correlate with the full-length gene or protein, for example, in an assay or other method of the invention. Biomarker expression can also be identified by detection of biomarker translation (i.e., detection of biomarker protein in a sample). Methods suitable for the detection of biomarker protein include any suitable method for detecting and/or measuring proteins from a cell or cell extract. Such methods include, but are not limited to, immunoblot (e.g., Western blot), enzyme-linked immunosorbent assay (ELISA), radioimmunoassay (MA), immunoprecipitation, immunohistochemistry and immunofluorescence. Particularly preferred methods for detection of proteins include any single-cell assay, including immunohistochemistry and immunofluorescence assays. Such methods are well known in the art. Furthermore, antibodies against certain of the biomarkers described herein are known in the art and are described in the public literature, and methods for their preparation are well known to the skilled worker.

The term "comparably" as used to compare expression of a test sample to a control sample shall mean indicia of like character and quantity and shall include, without limitation, values within one standard deviation around the mean value to which said comparison is made and values encompassing differential expression between the test sample and control sample.

The terms "differentially expressed gene," "differential gene expression," "differential expression" or "differentially expressed" and their synonyms, which are used interchangeably, refer to a gene whose expression is activated to a higher or lower level in a subject suffering from a disease, condition, or disorder, or as a result of the being administered a substance, drug, nutrient or dietary component or combinations thereof, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, condition, or disorder, or as a result of the being administered a substance, drug, nutrient or dietary component or combinations thereof, or between various stages of the same disease, condition, or disorder, or as a result of being administered different amounts of a substance, drug, nutrient or dietary component or combinations thereof. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about 2.0, 1.9, 1.8, 1.7, 1.6, 1.5, 1.4, 1.3, 1.2, 1.1 or 1.0-fold, preferably at least about two-fold or more, more preferably at least about 2.5, 3 or 4 or more fold change in the amount of transcribed polynucleotides or translated protein in a sample.

The term "fold" when used as a measure of differential gene expression means an amount of gene expression in a feline that is a multiple or a fraction of gene expression compared to the amount of gene expression in a comparison feline, e.g., a feline having symptoms related to hyperthyroidism, at risk for or having hyperthyroidism compared to an animal not demonstrating such a condition. For example, a gene that is expressed 2 times as much in the animal as in the comparison animal has a 2-fold differential gene expression and a gene that is expressed one-half as much in the animal as in the comparison animal also has a 2-fold differential gene expression.

The term "fragment" means (1) an oligonucleotide or polynucleotide sequence that is a portion of a complete sequence and that has the same or similar activity for a particular use as the complete polynucleotide sequence or (2) a peptide or polypeptide sequence that is a portion of a complete sequence and that has the same or similar activity for a particular use as the complete polypeptide sequence. Such fragments can comprise any number of nucleotides or amino acids deemed suitable for a particular use. Generally, oligonucleotide or polynucleotide fragments contain at least about 10, 50, 100, or 1000 nucleotides and polypeptide fragments contain at least about 4, 10, 20, or 50 consecutive amino acids from the complete sequence. The term encompasses polynucleotides and polypeptides variants of the fragments. A polynucleotide, for example, can be broken up, or fragmented into, a plurality of segments.

Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3rd Ed. Cold Spring Harbor Laboratory Press, Cold Spring Harbor, N.Y. (2001) ("Sambrook et al.), which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

The term "gene" or "genes" means a complete or partial segment of DNA involved in producing a polypeptide, including regions preceding and following the coding region (leader and trailer) and intervening sequences (introns) between individual coding segments (exons). The term encompasses any DNA sequence that hybridizes to the complement of gene coding sequences.

The term "homolog" means (1) a polynucleotide, including polynucleotides from the same or different animal species, having greater than 30%, 50%, 70%, 90%, 91%, 92%, 93%, 94%, 95%, 96%, 97%, 98% or 99% sequence similarity to a polynucleotide and having the same or substantially the same properties and performing the same or substantially the same function as the complete polynucleotide, or having the capability of specifically hybridizing to a polynucleotide under stringent conditions or (2) a polypeptide, including polypeptides from the same or different animal species, having greater than 30%, 50%, 70%, 90%, 91%, 92%, 93%, 94%, 95%, 96%, 97%, 98% or 99% sequence similarity to a polypeptide identified by the expression of polynucleotides and having the same or substantially the same properties and performing the same or substantially the same function as the complete polypeptide, or having the capability of specifically binding to a polypeptide identified by the expression of polynucleotides. Sequence similarity of two polypeptide sequences or of two polynucleotide sequences is determined using methods known to skilled artisans, e.g., the algorithm of Karlin and Altschul (Proc. Natl. Acad. Sci. USA 87:2264-2268 (1990)). Such an algorithm is incorporated into the NBLAST and XBLAST programs of Altschul et al. (J. Mol. Biol. 215:403-410 (1990)). To obtain gapped alignments for comparison purposes, Gapped Blast can be utilized as described in Altschul et al. (Nucl. Acids Res. 25: 3389-3402 (1997)). When utilizing BLAST and Gapped BLAST programs, the default parameters of the respective programs (e.g., XBLAST and NBLAST) are used. See http://www.ncbi.nlm.nih.gov.

The term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid." The proportion of the population of polynucleotides that forms stable hybrids is referred to herein as the "degree of hybridization."

Hybridization reactions can be performed in absolute or differential hybridization formats. In the absolute hybridization format, polynucleotides derived from one sample are hybridized to the probes in a nucleic acid array. Signals detected after the formation of hybridization complexes correlate to the polynucleotide levels in the sample. In the differential hybridization format, polynucleotides derived from two samples are labeled with different labeling moieties. A mixture of these differently labeled polynucleotides is added to a nucleic acid array. The nucleic acid array is then examined under conditions in which the emissions from the two different labels are individually detectable. In one embodiment, the fluorophores Cy3 and Cy5 (Amersham Pharmacia Biotech, Piscataway, N.J.) are used as the labeling moieties for the differential hybridization format.

Signals gathered from nucleic acid arrays can be analyzed using commercially available software, such as those provided by Affymetrix or Agilent Technologies. Controls, such as for scan sensitivity, probe labeling and cDNA or cRNA quantization, are preferably included in the hybridization experiments. Hybridization signals can be scaled or normalized before being subject to further analysis. For instance, hybridization signals for each individual probe can be normalized to take into account variations in hybridization intensities when more than one array is used under similar test conditions. Hybridization signals can also be normalized using the intensities derived from internal normalization controls contained on each array. In addition, genes with relatively consistent expression levels across the samples can be used to normalize the expression levels of other genes. In one embodiment, probes for certain maintenance genes are included in a nucleic acid array of the present invention. These genes are chosen because they show stable levels of expression across a diverse set of tissues. Hybridization signals can be normalized and/or scaled based on the expression levels of these maintenance genes.

The term "hybridization complex" means a complex that is formed between sample polynucleotides when the purines of one polynucleotide hydrogen bond with the pyrimidines of the complementary polynucleotide, e.g., 5'-A-G-T-C-3' base pairs with 3'-T-C-A-G-5'. The degree of complementarily and the use of nucleotide analogs affect the efficiency and stringency of hybridization reactions.

The term "hybridization probes" includes nucleic acids (such as oligonucleotides) capable of binding in a base-specific manner to a complementary strand of nucleic acid. Such probes include peptide nucleic acids, as described in Nielsen et al., Science 254:1497-1500 (1991), Nielsen Curr.

Opin. Biotechnol., 10:71-75 (1999) and other nucleic acid analogs and nucleic acid mimetics. See U.S. Pat. No. 6,156,501 filed Apr. 3, 1996.

"Nucleic acid sequence" means an oligonucleotide, nucleotide or polynucleotide, and fragments or portions thereof, and to DNA or RNA of genomic or synthetic origin which may be single- or double-stranded, and represent the sense or antisense strand.

The term "polynucleotide" or "oligonucleotide" means a polymer of nucleotides. The term encompasses DNA and RNA (including cDNA and mRNA) molecules, either single or double stranded and, if single stranded, its complementary sequence in either linear or circular form. The term also encompasses fragments, variants, homologs, and alleles, as appropriate for the sequences that have the same or substantially the same properties and perform the same or substantially the same function as the original sequence. The sequences may be fully complementary (no mismatches) when aligned or may have up to about a 30% sequence mismatch. Preferably, for polynucleotides, the chain contains from about 20 to 10,000 nucleotides, more preferably from about 150 to 3,500 nucleotides. Preferably, for oligonucleotides, the chain contains from about 2 to 100 nucleotides, more preferably from about 6 to 30 nucleotides. The exact size of a polynucleotide or oligonucleotide will depend on various factors and on the particular application and use of the polynucleotide or oligonucleotide. The term includes nucleotide polymers that are synthesized and that are isolated and purified from natural sources. The term "polynucleotide" is inclusive of "oligonucleotide."

The term "polypeptide," "peptide," or "protein" means a polymer of amino acids. The term encompasses naturally occurring and non-naturally occurring (synthetic) polymers and polymers in which artificial chemical mimetics are substituted for one or more amino acids. The term also encompasses fragments, variants, and homologs that have the same or substantially the same properties and perform the same or substantially the same function as the original sequence. The term encompass polymers of any length, preferably polymers containing from about 2 to 1000 amino acids, more preferably from about 5 to 500 amino acids. The term includes amino acid polymers that are synthesized and that are isolated and purified from natural sources.

The term "probe" means (1) an oligonucleotide or polynucleotide, either RNA or DNA, whether occurring naturally as in a purified restriction enzyme digest or produced synthetically, that is capable of annealing with or specifically hybridizing to a polynucleotide with sequences complementary to the probe or (2) a peptide or polypeptide capable of specifically binding a particular protein or protein fragment to the substantial exclusion of other proteins or protein fragments. An oligonucleotide or polynucleotide probe may be either single or double stranded. The exact length of the probe will depend upon many factors, including temperature, source, and use. For example, for diagnostic applications, depending on the complexity of the target sequence, an oligonucleotide probe typically contains about 10 to 100, 15 to 50, or 15 to 25 nucleotides. In certain diagnostic applications, a polynucleotide probe contains about 100-1000, 300-600, nucleotides, preferably about 300 nucleotides. The probes herein are selected to be "substantially" complementary to different strands of a particular target sequence. This means that the probes must be sufficiently complementary to specifically hybridize or anneal with their respective target sequences under a set of predetermined conditions. Therefore, the probe sequence need not reflect the exact complementary sequence of the target. For example, a noncomplementary nucleotide fragment may be attached to the 5' or 3' end of the probe, with the remainder of the probe sequence being complementary to the target sequence. Alternatively, noncomplementary bases or longer sequences can be interspersed into the probe provided that the probe sequence has sufficient complementarity with the sequence of the target polynucleotide to specifically anneal to the target polynucleotide. A peptide or polypeptide probe may be any molecule to which the protein or peptide specifically binds, including DNA (for DNA binding proteins), antibodies, cell membrane receptors, peptides, cofactors, lectins, sugars, polysaccharides, cells, cell membranes, organelles and organellar membranes.

The terms "sample" and "specimen" mean any animal tissue or fluid containing polynucleotides, including cells and other tissue containing DNA and RNA. Examples include: blood, kidney, connective, epithelial, lymphoid, muscle, nervous, sputum, and the like. A sample may be solid or liquid and that may contain DNA, RNA, cDNA, for example, bodily fluids such as blood or urine, cells, cell preparations or soluble fractions or media aliquots thereof, chromosomes, organelles, and the like.

The term "specifically bind" means a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

The term "specifically hybridize" means an association between two single stranded polynucleotides of sufficiently complementary sequence to permit such hybridization under predetermined conditions generally used in the art (sometimes termed "substantially complementary"). For example, the term may refer to hybridization of a polynucleotide probe with a substantially complementary sequence contained within a single stranded DNA or RNA molecule according to an aspect of the invention, to the substantial exclusion of hybridization of the polynucleotide probe with single stranded polynucleotides of non-complementary sequence.

The term "stringent conditions" means (1) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C., (2) hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42° C.; with washes at 42° C. in 0.2×SSC and 0.1% SDS or washes with 0.015 M NaCl, 0.0015 M sodium citrate, 0.1% Na2SO4 at 50° C. or similar art-recognized procedures employing similar low ionic strength and high temperature washing agents and similar denaturing agents.

The term "useful variations" means (1) for a polynucleotide, the complements of the polynucleotide; the homologs of the polynucleotide and its complements; the variants of the polynucleotide, its complements, and its homologs; and the fragments of the polynucleotide, its complements, its homologs, and its variants and (2) for a polypeptide, the homologs of the polypeptide; the variants of the polypeptide and its homologs; and the fragments of the polynucleotide, its homologs, and its variants.

The term "variant" means (1) a polynucleotide sequence containing any substitution, variation, modification, replacement, deletion, or addition of one or more nucleotides from or to a polynucleotide sequence and that has the same or substantially the same properties and performs the same or substantially the same function as the original sequence and (2) a polypeptide sequence containing any substitution, variation, modification, replacement, deletion, or addition of one or more amino acids from or to a polypeptide sequence and that has the same or substantially the same properties and performs the same or substantially the same function as the original sequence. The term therefore includes single nucleotide polymorphisms (SNPs) and allelic variants and includes conservative and non-conservative amino acid substitutions in polypeptides. The term also encompasses chemical derivatization of a polynucleotide or polypeptide and substitution of nucleotides or amino acids with nucleotides or amino acids that do not occur naturally, as appropriate.

Unless defined otherwise, all technical and scientific terms and any acronyms used herein have the same meanings as commonly understood by one of ordinary skill in the art in the field of the invention.

Probes

The probes useful in the practice of the invention and which are utilized in the identification of the feline biomarkers in the feline samples correspond to the following probe identification numbers used in the proprietary feline gene chip manufactured by Affymetrix, identified as Affymetrix Feline GeneChip®, as more fully described in this specification.

Other and further objects, features, and advantages of the present invention will be readily apparent to those skilled in the art.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 5 should be considered to have specifically disclosed subranges such as from 1 to 3, from 1 to 4, from 2 to 4, from 2 to 5, from 3 to 5 etc., as well as individual numbers within that range, for example, 1, 2, 3, 4, and 5. This applies regardless of the breadth of the range The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as: Genome Analysis: A Laboratory Manual Series (Vols. I-IV); Using Antibodies: A Laboratory Manual; Cells: A Laboratory Manual; PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000); Lehninger, Principles of Biochemistry 3rd Ed., W.H. Freeman Pub., New York, N.Y.; and Berg et al. (2002) Biochemistry, 5th Ed., W.H. Freeman Pub., New York, N.Y., all of which are herein incorporated in their entirety by reference for all purposes.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248, 6,309,822 and 6,344,316. Genotyping and uses therefore are shown in U.S. Ser. No. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

Those skilled in the art will recognize that the products and methods embodied in the present invention may be applied to a variety of systems, including commercially available gene expression monitoring systems involving nucleic acid probe arrays, membrane blots, microwells, beads and sample tubes, constructed with various materials using various methods known in the art. Accordingly, the present invention is not limited to any particular environment, and the following description of specific embodiments of the present invention is for illustrative purposes only.

The gene expression monitoring system, in a preferred embodiment, may comprise a nucleic acid probe array (including an oligonucleotide array, a cDNA array, a spotted array, and the like), membrane blot (such as used in hybridization analysis such as Northern, Southern, dot, and the like), or microwells, sample tubes, beads or fibers (or any solid support comprising bound nucleic acids). See U.S. Pat. Nos. 5,770,722, 5,744,305, 5,677,195, 5,445,934 and 6,040,193 which are incorporated herein by reference. The gene expression monitoring system may also comprise nucleic acid probes in solution.

The present invention also contemplates sample preparation involving amplification. A genomic sample may be amplified by a variety of mechanisms, some of which may employ PCR. See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP- PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517 and 6,063,603, each of which is incorporated herein by reference). Other amplification methods that may be used are described in, U.S. Pat. Nos. 5,242,794, 5,494,810, 4,988,617, 6,344,316 and in U.S. Ser. No. 09/854,317, each of which is incorporated herein by reference.

Additional methods of sample preparation and techniques are described in Dong et al., Genome Research 11, 1418 (2001), in U.S. Pat. Nos. 6,361,947, 6,391,592 and U.S. patent application Ser. Nos. 09/916,135, 09/920,491, 09/910,292 and 10/013,598.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue. In a preferred embodiment, the proportional amplification methods of the present invention can provide reproducible results (i.e., within statistically significant margins of error or degrees of confidence) sufficient to facilitate the measurement of quantitative as well as qualitative differences in the tested samples.

Polynucleotide hybridization assays are well known in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S., 80: 1194 (1983). Methods and apparatus for carrying out repeated and controlled hybridization reactions have been described in U.S. Pat. Nos. 5,871,928, 5,874,219, 6,045,996, 6,386,749 and 6,391,623 each of which are incorporated herein by reference. Signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803 and 6,225,625, in U.S. Patent application 60/364,731 and in PCT Application PCT/US99/06097 (published as WO99/47964), each of which also is hereby incorporated by reference in its entirety for all purposes. Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

The invention is not limited to the particular methodology, protocols, and reagents described herein because they may vary. Further, the terminology used herein is for the purpose of describing particular embodiments only and is not intended to limit the scope of the present invention.

In one embodiment, the present invention encompasses one or more genes or gene segments ("genes" as defined herein) that are differentially expressed in abnormal animals compared to normal animals. The invention is based upon the discovery of polynucleotides that are differentially expressed in abnormal animals compared to normal animals. The genes are identified by comparing the expression of genes in tissue samples taken from animals diagnosed as abnormal with genes in tissue samples from animals diagnosed as normal using Affymetrix GeneChip® technology.

The polynucleotides and genes are identified by measuring differences in gene expression from tissue samples taken from felines diagnosed as abnormal and having a thyroid disorder with gene expression in tissue samples from felines diagnosed as normal. Changes in gene expression can be determined by any method known to skilled artisans. Generally, changes in gene expression are determined by measuring transcription (determining the amount of mRNA produced by a gene) or measuring translation (determining the amount of protein produced by a gene). The amount of RNA or protein produced by a gene can be determined using any method known to skilled artisans for quantifying polynucleotides and proteins.

Generally, mRNA expression is determined using polymerase chain reaction (PCR) (including, without limitation, reverse transcription-PCR (RT-PCR) and quantitative real-time PCR (qPCR)), short or long oligonucleotide arrays, cDNA arrays, EST sequencing, Northern blotting, SAGE, MPSS, MS, bead arrays and other hybridization methods. The RNA measured is typically in the form of mRNA or reverse transcribed mRNA.

Protein or polypeptide expression is determined using various colorimetric and spectroscopic assays and methods such as quantitative Western blots, ELISA, 2D-gels, gas or liquid chromatography, mass-spec, the lowry assay, the biuret assay, fluorescence assays, turbidimetric methods, the bicinchoninic assay, protein chip technology, infrared absorbance, ninhydrin, the Bradford assay, and ultraviolet absorbance.

Gene chips allow a large-scale study of biological processes and the measurement of activity within a cell at a certain point in time. Microarray analysis permits one to account for differences in phenotypes on a large-scale genetic basis. Actual measurement of gene expression products is a more accurate indicator of gene function than determining sequences per se. Microarray analysis is based upon quantifying the concentration of a gene's mRNA transcript in a cell at a given time. DNA is immobilized on a medium and labeled target mRNA is hybridized with probes on the array. Binding of the labeled mRNA to the probes is measured by laser analysis. The measurement is a count of photons emitted. The entire chip is scanned and digitally imaged. The image is processed to locate probes and to assign intensity measurements to each probe. In this manner up- and down-regulated genes may be determined. The analysis enables the skilled person to find groups of genes with similar expression profiles and to determine tissues with similar expression profiles. In this manner, genes that explain the observed differences in tissue samples can be identified.

Affymetrix Gene Chips typically employ probes of 25 bp and probe sets of 11 to 20 probes corresponding to a particular gene or EST. The chip is constructed with a perfect match and mismatch probe of 25 bp each, the former being perfectly complementary to a specific region of a gene and the latter having the $13^{th}$ bp substituted to make a mismatch. A probe summarization algorithm is used to determine background correction, normalization and probe summarization, which is the conversion of probe values to probe set expression values. RMA is one of the algorithms that may be used for this purpose. The algorithm performs the last two steps of analysis, normalization and summarization of probe-level intensity measurements. The perfect match values are, therefore, background corrected, normalized and summarized into a set of expression measurements.

The raw data is analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

Generally, differential gene expression in abnormal animals compared to normal animals is determined by measuring the expression of at least one gene. Preferably, the expression of two or more differentially expressed genes is measured to provide a gene expression pattern or gene expression profile. More preferably, the expression of a plurality of differentially expressed genes is measured to provide additional information for a more significant gene expression pattern or profile.

The present invention provides a plurality of markers that together or alone are or can be used as markers of renal disease. In especially useful embodiments of the invention, a plurality of these markers can be selected and their mRNA expression may be measured simultaneously to provide expression profiles for use in various aspects of the inventions described in this application.

In another aspect, the invention provides a device suitable for detecting the expression of a plurality of genes differentially expressed in abnormal felines compared to normal felines. The device comprises a substrate having a plurality of the oligonucleotide or polynucleotide probes of the present invention affixed to the substrate at known locations. The device is essentially an immobilized version of the oligonucleotide or polynucleotide probes described herein. The device is useful for rapid and specific detection of genes and polynucleotides and their expression patterns and profiles. Typically, such probes are linked to a substrate or similar solid support and a sample containing one or more polynucleotides (e.g., a gene, a PCR product, a ligase chain reaction (LCR) product, a DNA sequence that has been synthesized using amplification techniques, or a mixture thereof) is exposed to the probes such that the sample polynucleotide(s) can hybridize to the probes. The probes, the sample polynucleotide(s), or both, are labeled, typically with a fluorophore or other tag such as streptavidin, and detected using methods known to skilled artisans. If the sample polynucleotide(s) is labeled, hybridization may be detected by detecting bound fluorescence. If the probes are labeled, hybridization is typically detected by label quenching. If both the probe and the sample polynucleotide(s) are labeled, hybridization is typically detected by monitoring a color shift resulting from proximity of the two bound labels. A variety of labeling strategies and labels are known to skilled artisans, particularly for fluorescent labels. Preferably, the probes are immobilized on substrates suitable for forming an array (known by several names including DNA microarray, gene chip, biochip, DNA chip, and gene array) comparable to those known in the art.

Methods for determining the amount or concentration of protein in a sample are known to skilled artisans. Such methods include radioimmunoassays, competitive-binding assays, Western blot analysis, and ELISA assays. For methods that use antibodies, polyclonal and monoclonal antibodies are suitable. Such antibodies may be immunologically specific for a protein, protein epitope, or protein fragment.

Some embodiments of the invention utilize antibodies for the detection and quantification of proteins produced by expression of the polynucleotides of the present invention. Although proteins may be detected by immunoprecipitation, affinity separation, Western blot analysis, protein arrays, and the like, a preferred method utilizes ELISA technology wherein the antibody is immobilized on a solid support and a target protein or peptide is exposed to the immobilized antibody. Either the probe, or the target, or both, can be labeled using known methods.

In a further aspect, the invention provides a method for detecting the differential expression of one or more genes differentially expressed in abnormal felines compared to normal felines in a sample. The method comprises (a) hybridizing a combination comprising a plurality of polynucleotide probes that are differentially expressed in abnormal felines compared to normal felines with polynucleotides in the sample to form one or more hybridization complexes; (b) optionally, hybridizing a combination comprising a plurality of polynucleotide probes that are differentially expressed in abnormal felines compared to normal felines with polynucleotides in a standard to form one or more hybridization complexes; (c) detecting the hybridization complexes from the sample and, optionally, the standard from step (b); and (d) comparing the hybridization complexes from the sample with the hybridization complexes from a standard, wherein a difference in the amount of hybridization complexes between the standard and sample indicate differential expression of genes differentially expressed in abnormal animals compared to normal animals in the sample.

Step (b) and part of step (c) are optional and are used if a relatively contemporaneous comparison of two or more test systems is to be conducted. However, in a preferred embodiment, the standard used for comparison is based upon data previously obtained using the method.

These probes are exposed to a sample to form hybridization complexes that are detected and compared with those of a standard. The differences between the hybridization complexes from the sample and standard indicate differential expression of polynucleotides and therefore genes differentially expressed in abnormal felines compared to normal felines in the sample. In a preferred embodiment, probes are made to specifically detect polynucleotides or fragments thereof produced by one or more of the genes or gene fragments identified by the present invention. Methods for detecting hybridization complexes are known to skilled artisans.

In another aspect, the invention provides a method for detecting the differential expression of genes differentially expressed in abnormal felines compared to normal felines in a sample. The method comprises (a) reacting a combination comprising a plurality of polypeptide probes with proteins in the sample under conditions that allow specific binding between the probes and the proteins to occur, wherein the proteins bound by the probes are differentially expressed in an abnormal feline compared to a normal feline; (b) optionally, reacting a combination comprising a plurality of polypeptide probes with proteins in a standard under conditions that allow specific binding between the probes and the proteins to occur, wherein the proteins bound by the probes are differentially expressed in an abnormal feline compared to a normal feline; (c) detecting specific binding in the sample and, optionally, the standard from step (b); and (d) comparing the specific binding in the sample with that of a standard, wherein differences between the specific binding in the standard and the sample indicate differential expression of genes differentially expressed in abnormal felines compared to normal felines in the sample.

These probes are exposed to a sample to form specific binding that is detected and compared with those of a standard. The differences between the specific binding from the sample and standard indicate differential expression of proteins and therefore genes differentially expressed in abnormal felines compared to normal felines, particularly abnormal-associated genes, in the sample. In a preferred embodiment, probes are made to specifically detect proteins or fragments thereof produced by one or more of the genes or gene fragments identified by the present invention.

In one embodiment, the method further comprises exposing the feline or sample to a test substance before reacting the polypeptides with the proteins. Then, the comparison is indicative of whether the test substance altered the expression of genes differentially expressed in abnormal felines compared to normal felines, particularly abnormal-associated genes, in the sample.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Example 1—Gene Expression in Hyperthyroid Felines

This study focuses on gene expression in thyroid tissue and whole blood in felines with hyperthyroidism. All hyperthyroid felines are diagnosed by veterinarians on the basis of clinical signs and elevated T4 concentrations. In the tissue study, 1308 significant differential expression genes are found between hyperthyroid felines and non-hyperthyroid felines with FDR=0.1 and fold change of >=+/−1.25. In the whole blood study, 1094 significant genes are found between hyperthyroid felines and non-hyperthyroid felines with the same cutoff as shown above. In the tissue study, all the genes known to be involved in the pathway leading to the production of thyroid hormones are found to be up-regulated in the hyperthyroid felines. The increased expression of these genes clearly contributes to a high T4 production in the feline body. In the whole blood study, 60 genes are found to overlap with those found from the solid tissue work that appear to be regulated in the same direction as seen in the tissue study. By using these 60 genes, the hyperthyroid felines can be distinguished from the normal felines as tested in the whole blood, as well as in the tissue.

Felines are divided into two groups. One group includes felines with no evidence of disease, and the other group includes felines with hyperthyroidism. Both tissues and whole blood are collected for gene expression analysis.

RNA Isolation from Solid Tissue:
Tissue samples are homogenized using the Ultra-Turrax T25 Power Homogenizer. RNA is isolated using the protocol outlined in SOP # LAB-LS-028.3. The RNA quality and quantity is determined by using the Agilent 2100 Bioanalyzer (Agilent Technologies) according to the manufacturer's instructions. RNA integrity is determined by using the RNA integrity number (RIN; Agilent 2100 RIN Beta Version Software). Purified RNA samples are stored at −70° C.

Sample Preparation from Whole Blood:
Blood is collected and processed according to the manufacturer's instructions in PAXgene RNA blood tubes. The PAXgene RNA blood tubes are stored at −20° C. (short-term storage, <6 months) and −70° C. (>6 months) before RNA is isolated.

RNA Isolation from Whole Blood:
RNA is isolated with the PAXgene Blood RNA Isolation Kit according to the manufacturer's instructions (Qiagen, p/n 762164). The RNA quality and quantity is determined using the Agilent 2100 Bioanalyzer (Agilent Technologies) according to the manufacturer's instructions. RNA integrity is determined by using the RNA integrity number (RIN; Agilent 2100 RIN Beta Version Software). Purified RNA samples are stored at −70° C.

Whole Blood Probe Preparation:
Labeling and amplification reagents are obtained from NuGEN Technologies, Inc (San Carlos, Calif., USA) and biotinylated cDNA targets are prepared according to manufacturer's instructions. Double-stranded cDNA is synthesized from approximately 75 ng of total RNA, followed by a linear isothermal amplification (SPIA Amplification™) step to produce single-stranded cDNA. Fragmentation is followed by a direct labeling process that attached biotin to the amplified probe. Probe purifications are performed using DNA Clean and Concentrator-25 (Zymo Research, Orange, C-A, USA).

Solid Tissue Probe Preparation:
Labeling and amplification reagents are obtained from Affymetrix (3420 Central Expressway, Santa Clara, Calif. 95051). The One-cycle cDNA Synthesis Kit (p/n 900431) and 3'IVT Labeling Kit (p/n 900449) is used to synthesize, fragment and label each cDNA target. All cDNA targets are prepared according to manufacturer's instructions. Probe purifications are performed using the GeneChip Sample Cleanup Module (Affymetrix p/n 900371). It is important to note that Affymetrix no longer sells these exact products, per se, as they have reformulated and renamed their labeling and amplification product line, but equivalent products are available.

Array Hybridization and Processing (Whole Blood):
After pre-hybridization for 20 minutes at 45° C., 1.5 µg of each target cDNA is mixed with Affymetrix hybridization controls in hybridization buffer and hybridized with the Feline-2 GeneChip® for 16 hours at 45° C. After the hybridization cocktails are removed, the chips are washed in a fluidics station with low-stringency buffer (6× standard saline phosphate with EDTA, 0.01% Tween 20) and high stringency buffer (100 mM N-morpholino-ethanesulfonic acid (MES), 0.1 M NaCl, and 0.01% Tween 20) and stained with SAPE (streptavidin phycoerythrin). This process is followed by incubation with normal goat IgG and biotinylated mouse anti-streptavidin antibody (Vector Lab, BA-0500) followed by re-staining with SAPE. The chips are scanned in a GeneChip® Scanner 3000 7G (Affymetrix Inc, Santa Clara, Calif.) to detect hybridization signals. Image inspection is performed manually immediately following each scan (GeneChip® Expression Analysis Technical Manual. P/N 702232 Rev. 3, Chapter II and III).

Array Hybridization and Processing (Solid Tissues):
After pre-hybridization for 10 minutes at 45° C., 4.4 µg of each target cDNA is mixed with Affymetrix hybridization controls in a hybridization buffer and hybridized with the Feline-2 GeneChip® for 16-18 hours at 45° C. After the hybridization cocktails are removed, the chips are washed in a fluidics station with low-stringency buffer (6× standard saline phosphate with EDTA, 0.01% Tween 20) and high stringency buffer (100 mM N-morpholino-ethanesulfonic acid (MES), 0.1 M NaCl, and 0.01% Tween 20) and stained with SAPE (streptavidin phycoerythrin). This process is followed by incubation with normal goat IgG and biotinylated mouse anti-streptavidin antibody (Vector Lab, BA-0500) followed by re-staining with SAPE. The chips are scanned in a GeneChip® Scanner 3000 7G (Affymetrix Inc, Santa Clara, Calif.) to detect hybridization signals. Image inspection is performed manually immediately following each scan (GeneChip® Expression Analysis Technical Manual. P/N 702232 Rev. 3, Chapter II and III).

Data Analysis:

The Partek® GS (Partek Inc., St. Charles, Mo.) for Gene Expression Data software (Partek Incorporated, 12747 Olive Blvd., Suite 205, St. Louis, Mo. 63141, U.S.A. http://www.partek.com/partekgs_geneexpression) is used for data analysis. The Robust Multichip Average (RMA) algorithm (Rafael. A. Irizarry, Benjamin M. Bolstad, Francois Collin, Leslie M. Cope, Bridget Hobbs and Terence P. Speed (2003), Summaries of Affymetrix GeneChip probe level data Nucleic Acids Research 31(4):e15) is used for background adjustment, normalization, and probe-level summarization of the GeneChip® samples. The ANOVA analysis is performed to find significant differentially expressed genes between any two groups with a minimal FDR control at 0.1 and a fold change of 1.25 in each direction. Our empirical studies have revealed that the Feline-2 GeneChips® have an associated background noise level of 1.3 fold. Therefore, all analyses presented in this report employed a +/−1.25 fold cut-off (to be more inclusive). Furthermore, the false discovery rate threshold of 0.1 (means that 10% of observations are due to chance) is chosen as the minimum level of acceptable statistical significance.

This study focuses on gene expression in thyroid tissue and whole blood with respect to feline hyperthyroidism. In the tissue study, 1308 genes are found to be significantly differentially expressed between hyperthyroid felines and non-hyperthyroid felines with FDR=0.1 and fold change >=+/−1.25. In the whole blood study, 1094 significant genes are identified using the same cutoffs.

PCA analysis of both studies demonstrate that based on differential gene expression, the hyperthyroid felines are clustered together and are separate from the non-hyperthyroid felines.

Feline hyperthyroidism is an endocrine disorder that involves the production of too much thyroid hormone by the thyroid gland. This condition tends to affect middle-aged and older felines, and both males and females are equally at risk of developing this disorder. Hyperthyroidism affects every organ and cell in a feline's body (1).

The level of the thyroid hormone thyroxin (T4) is measured in the blood. High levels of this hormone are very indicative of hyperthyroidism. In the majority of felines suffering from this endocrine disorder, T4 levels will be so high that there will be no question that hyperthyroidism is the problem. However, on some occasions a feline's hormone levels will fall within the upper levels of the normal range. In such cases, a further test known as a Free T4 (FT4) will be performed. In most cases, this second thyroid test is enough to confirm a diagnosis of hyperthyroidism.

Also, blood tests will reveal elevated levels of red blood cells and leukocytes along with low levels of lymphocytes and eosinophils. Also, some felines with hyperthyroidism will have elevated levels of ALT. Other substances may be present in elevated levels as well, such as other enzymes, the chemical creatinine, phosphorus, and the bile pigment bilirubin. Some of these higher than normal levels are triggered by physiological complications that arise from hyperthyroidism.

A feline's thyroid is a butterfly-shaped gland located in their neck. This gland is responsible for producing the hormone thyroxin (T4), which plays a significant role in regulating a body's metabolic rate. All organs and physiological systems are affected by hyperthyroidism, causing classic symptoms such as weight loss, hyperactivity, increased blood pressure, and an elevated heart rate.

In the tissue study, all of the genes involved in the pathway leading to the production of thyroid hormones are found to be up-regulated in the hyperthyroid felines. The genes are those found in Table A. The increased expression of these genes contribute to a high T4 production in feline body.

Description of Up-Regulated Genes that Contribute to Thyroid Hormone Over Production:

IYD (4.55 fold increase) This gene encodes an enzyme that catalyzes the oxidative NADPH-dependent deiodination of mono- and diiodotyrosine, which are the halogenated byproducts of thyroid hormone production. The N-terminus of the protein functions as a membrane anchor. Mutations in this gene cause congenital hypothyroidism due to dyshormonogenesis type 4, which is also referred to as deiodinase deficiency, or iodotyrosine dehalogenase deficiency, or thyroid hormonogenesis type 4.

TG (2.02 fold increase) Thyroglobulin (Tg) is a glycoprotein homodimer produced predominantly by the thyroid gland. It acts as a substrate for the synthesis of thyroxine and triiodothyronine as well as the storage of the inactive forms of thyroid hormone and iodine. Thyroglobulin is secreted from the endoplasmic reticulum to its site of iodination, and subsequent thyroxine biosynthesis, in the follicular lumen. Mutations in this gene cause thyroid dyshormonogenesis, manifested as goiter, and are associated with moderate to severe congenital hypothyroidism.

SLC5A5, NIS (4.6 fold increase) This gene encodes a member of the sodium glucose cotransporter family. The encoded protein is responsible for the uptake of iodine in tissues such as the thyroid and lactating breast tissue. The iodine taken up by the thyroid is incorporated into the metabolic regulators triiodothyronine (T3) and tetraiodothyronine (T4). Mutations in this gene are associated with thyroid dyshormonogenesis 1.

TPO (4.06 fold increase) This gene encodes a membrane-bound glycoprotein. The encoded protein acts as an enzyme and plays a central role in thyroid gland function. The protein functions in the iodination of tyrosine residues in thyroglobulin and phenoxy-ester formation between pairs of iodinated tyrosines to generate the thyroid hormones, thyroxine and triiodothyronine. Mutations in this gene are associated with several disorders of thyroid hormonogenesis, including congenital hypothyroidism, congenital goiter, and thyroid hormone organification defect IIA.

TSHR (2.2 fold increase) The protein encoded by this gene is a membrane protein and a major controller of thyroid cell metabolism. The encoded protein is a receptor for thyrothropin and thyrostimulin, and its activity is mediated by adenylate cyclase. Defects in this gene are a cause of several types of hyperthyroidism.

DUOX2, ThOX (1.55 fold increase) The protein encoded by this gene is a glycoprotein and a member of the NADPH oxidase family. The synthesis of thyroid hormone is catalyzed by a protein complex located at the apical membrane of thyroid follicular cells. This complex contains an iodide transporter, thyroperoxidase, and a peroxide generating system that includes this encoded protein and DUOX1. This protein is known as dual oxidase because it has both a peroxidase homology domain and a gp91phox domain.

In hyperthyroid feline tissue study, several genes involved in the arachidonic acid production pathway are up regulated. Most of those genes are upstream genes as related to arachidonic acid synthesis, therefore, the production of arachidonic acid could be increased. Indeed, in human studies, it has been found that the arachidonic acid levels are significantly higher in the hyperthyroid than either normal or in the hypothyroid group of people. Arachidonic acid is a polyunsaturated fatty acid that is present in the phospholipids (especially phosphatidylethanolamine, phosphatidylcholine and phosphatidylinositides) of membranes of the body's cells, and is abundant in the brain, muscles, liver. In addition to being involved in cellular signaling as a lipid second messenger involved in the regulation of signaling enzymes, such as PLC-γ, PLC-δ and PKC-α, -β and -γ isoforms, arachidonic acid is a key inflammatory intermediate. Arachidonic acid plays a central role in inflammation related to injury and many diseased states. How it is metabolized in the body dictates its inflammatory or anti-inflammatory activity. Individuals suffering from joint pains or active inflammatory disease may find that increased arachidonic acid consumption exacerbates symptoms, probably because it is being more readily converted to inflammatory compounds. Likewise, high arachidonic acid consumption is not advised for individuals with a history of inflammatory disease, or that are in compromised health. It is also of note that while ARA supplementation does not appear to have pro-inflammatory effects in healthy individuals, it may counter the anti-inflammatory effects of omega-3 EFA supplementation. Therefore, in hyperthyroid felines, diet should be formatted to avoid arachidonic acid.

TABLE 2

Genes in Arachidonic Acid Production Pathway are Up-Regulated in the Tissue

| IDs | Signal HT/normal | Gene Symbol | Gene Name |
| --- | --- | --- | --- |
| HP06563_at | 4.36 | PA24A, cPLA2, PLA | phospholipase A2, group IVA (cytosolic, calcium-dependent) |
| HP16072_at; HP05605_at | 2.4 | ACSL5 | acyl-CoA synthetase long-chain family member 5 |
| HP03050_at | 1.62 | PPT1 | palmitoyl-protein thioesterase 1 |
| HP08203_at | 1.46 | LIPE | lipase, endothelial |
| HP07277_at | 1.32 | ACSL3 | acyl-CoA synthetase long-chain family member 3 |

In the whole blood gene expression study, 60 genes are found to overlap with those found in the tissue analysis and exhibit the same direction of regulation. However, none of those genes found to be associated with thyroid hormone production as seen in the tissue study. By using these 60 genes, the hyperthyroid felines can be distinguished from the normal ones as tested in the blood, as well as in the tissue at the same time. The 60 genes are those found in Table B.

The invention claimed is:

1. A method of treating a feline suffering from hyperthyroidism, the method comprising:
measuring an increase of at least a three fold change in the level of expression of one or more biomarkers in a sample from a feline to a control value for expression in a sample from a normal feline or population of felines, and/or relative to a previous individual baseline value from the feline;
identifying the feline having an increase of at least three fold change in the level of expression as suffering from hyperthyroidism; and
treating the feline identified as suffering from hyperthryoidism by dietary intervention,
wherein treating the feline by dietary intervention comprises feeding the feline a diet comprising iodine in an amount of less than 0.35 mg/kg, selenium in an amount of less than 0.1 mg/kg, and/or arachidonic acid in an amount of less than or equal to 0.2%, and
wherein the one or more biomarkers exhibiting the increase in the level of expression comprises TPO.

2. The method of claim 1, wherein measuring the increase of at least a three fold change in the level of expression of the one or more biomarkers comprises utilizing a microarray or a polymerase chain reaction:
wherein the microarray is a DNA microarray comprising one or more oligonucleotides complimentary to mRNA or cDNA corresponding to the one or more biomarkers to be measured, or
wherein the polymerase chain reaction is a quantitative polymerase chain reaction with oligonucleotide primers for mRNA or cDNA corresponding to the one or more biomarkers to be measured.

3. The method of claim 1, wherein measuring the increase of at least a three fold change in the level of expression of the one or more biomarkers comprises:
isolating RNA from the sample,
reverse transcribing the RNA to obtain the corresponding cDNA,
isolating and fragmenting the cDNA thus obtained,
contacting the cDNA fragments with a DNA microarray comprising one or more oligonucleotides complementary to cDNA corresponding to the one or more biomarkers to be measured, and
detecting hybridization between the cDNA fragments and the one or more oligonucleotides in the DNA microarray.

4. The method of claim 3, wherein the hybridization between the cDNA fragments and the one or more oligonucleotides in the DNA microarray is under stringent conditions.

5. The method of claim 1, wherein the level of expression of the biomarker is detected by an antibody to the expressed protein.

6. The method of claim 1, wherein the level of expression of the biomarker is detected by measuring the amount of protein in the sample using quantitative mass spectroscopy.

7. The method of claim 1, wherein the level of expression is measured for at least five biomarkers from the same sample.

8. The method of claim 1, wherein the sample is blood or a thyroid tissue.

9. A method of treating a feline suffering from hyperthyroidism, the method comprising:
measuring an increase of at least a three fold change in the level of expression of one or more biomarkers in a sample from a feline to a control value for expression in a sample from a normal feline or population of felines, and/or relative to a previous individual baseline value from the feline; and
identifying the feline having an increase of at least three fold change in the level of expression as suffering from hyperthyroidism; and
treating the feline identified as suffering from hyperthyroidism by pharmaceutical intervention, wherein treating the feline by pharmaceutical intervention comprises administering an effective amount of a drug which inhibits production of T-4, administering radioiodine therapy, and/or performing a surgical thyroidectomy, and wherein the one or more biomarkers exhibiting the increase in the level of expression comprises TPO.

10. The method of claim 9, wherein measuring the increase of at least a three fold change in the level of expression of the one or more biomarkers comprises utilizing a microarray or a polymerase chain reaction:

wherein the microarray is a DNA microarray comprising one or more oligonucleotides complimentary to mRNA or cDNA corresponding to the one or more biomarkers to be measured, or wherein the polymerase chain reaction is a quantitative polymerase chain reaction with oligonucleotide primers for mRNA or cDNA corresponding to the one or more biomarkers to be measured.

11. The method of claim 9, wherein measuring the increase of at least a three fold change in the level of expression of the one or more biomarkers comprises:

isolating RNA from the sample, reverse transcribing the RNA to obtain the corresponding cDNA, isolating and fragmenting the cDNA thus obtained, contacting the cDNA fragments with a DNA microarray comprising one or more oligonucleotides complementary to cDNA corresponding to the one or more biomarkers to be measured, and detecting hybridization between the cDNA fragments and the one or more oligonucleotides in the DNA microarray.

12. The method of claim 9, wherein the level of expression of the biomarker is detected by an antibody to the expressed protein.

13. The method of claim 9, wherein the level of expression of the biomarker is detected by measuring the amount of protein in the sample using quantitative mass spectroscopy.

14. The method of claim 9, wherein the sample is blood or thyroid tissue.

15. A method of treating a feline suffering from hyperthyroidism, the method comprising:

measuring an increase of at least a three fold change in the level of expression of one or more biomarkers in a sample from a feline to a control value for expression in a sample from a normal feline or population of felines, and/or relative to a previous individual baseline value from the feline; and identifying the feline having an increase of at least three fold change in the level of expression as suffering from hyperthyroidism; and treating the feline identified as suffering from hyperthyroidism by pharmaceutical intervention, wherein treating the feline by pharmaceutical intervention comprises administering a drug selected from methimazole or carbimazole, and wherein the one or more biomarkers exhibiting the increase in the level of expression comprises TPO.

16. The method of claim 15, wherein measuring the increase of at least a three fold change in the level of expression of the one or more biomarkers comprises utilizing a microarray or a polymerase chain reaction:

wherein the microarray is a DNA microarray comprising one or more oligonucleotides complimentary to mRNA or cDNA corresponding to the one or more biomarkers to be measured, or wherein the polymerase chain reaction is a quantitative polymerase chain reaction with oligonucleotide primers for mRNA or cDNA corresponding to the one or more biomarkers to be measured.

17. The method of claim 15, wherein measuring the increase of at least a three fold change in the level of expression of the one or more biomarkers comprises:

isolating RNA from the sample, reverse transcribing the RNA to obtain the corresponding cDNA, isolating and fragmenting the cDNA thus obtained, contacting the cDNA fragments with a DNA microarray comprising one or more oligonucleotides complementary to cDNA corresponding to the one or more biomarkers to be measured, and detecting hybridization between the cDNA fragments and the one or more oligonucleotides in the DNA microarray.

18. The method of claim 15, wherein the level of expression of the biomarker is detected by an antibody to the expressed protein.

19. The method of claim 15, wherein the level of expression of the biomarker is detected by measuring the amount of protein in the sample using quantitative mass spectroscopy.

20. The method of claim 15, wherein the sample is blood or thyroid tissue.

\* \* \* \* \*

UNITED STATES PATENT AND TRADEMARK OFFICE
CERTIFICATE OF CORRECTION

PATENT NO. : 10,704,102 B2
APPLICATION NO. : 16/184396
DATED : July 7, 2020
INVENTOR(S) : Samer Waleed Khedheyer Al-Murrani et al.

It is certified that error appears in the above-identified patent and that said Letters Patent is hereby corrected as shown below:

On the Title Page

In Column 1, item (56) under "U.S. PATENT DOCUMENTS", Line 4, delete "Mullis" and insert -- Mullis et al. --, therefor.

In Column 2, item (56) under "FOREIGN PATENT DOCUMENTS", Line 3, delete "WO 9006995" and insert -- WO 90/06995 --, therefor.

On Page 2, in Column 1, item (56) under "OTHER PUBLICATIONS", Line 11, delete "eats" and insert -- cats --, therefor.

On Page 2, Column 1, item (56) under "OTHER PUBLICATIONS", Line 33, delete "Anonymous" and insert -- Anonymous; --, therefor.

On Page 2, Column 1, item (56) under "OTHER PUBLICATIONS", Line 37, delete "67(12)11253-1255." and insert -- 67(12):1253-1255. --, therefor.

On Page 2, in Column 2, item (56) under "OTHER PUBLICATIONS", Line 7, delete "culi" and insert -- coli --, therefor.

On Page 2, in Column 2, item (56) under "OTHER PUBLICATIONS", Line 20, delete "INrf22" and insert -- INrf2 --, therefor.

On Page 2, in Column 2, item (56) under "OTHER PUBLICATIONS", Line 61, delete "73:1279-1281." and insert -- 73:1279-1283. --, therefor.

On Page 2, in Column 2, item (56) under "OTHER PUBLICATIONS", Line 65, delete "Doeosahexaenoate" and insert -- Docosahexaenoate --, therefor.

Signed and Sealed this
Twenty-second Day of September, 2020

Andrei Iancu
*Director of the United States Patent and Trademark Office*

CERTIFICATE OF CORRECTION (continued)
U.S. Pat. No. 10,704,102 B2

On Page 3, in Column 1, item (56) under "OTHER PUBLICATIONS", Line 10, delete "Hepaincytes" and insert -- Hepatocytes --, therefor.

On Page 3, in Column 1, item (56) under "OTHER PUBLICATIONS", Line 26, delete "Hepatoeyte" and insert -- Hepatocytes --, therefor.

On Page 3, in Column 1, item (56) under "OTHER PUBLICATIONS", Line 31, delete "Chemoproteetion" and insert -- Chemoprotection --, therefor.

On Page 3, in Column 1, item (56) under "OTHER PUBLICATIONS", Line 32, delete "Mel" and insert -- Mol --, therefor.

On Page 3, in Column 1, item (56) under "OTHER PUBLICATIONS", Lines 38-39, delete "PCT/US20122/042534" and insert -- PCT/US2012/042534 --, therefor.

On Page 3, in Column 1, item (56) under "OTHER PUBLICATIONS", Line 50, delete "or" and insert -- of --, therefor.

On Page 3, in Column 2, item (56) under "OTHER PUBLICATIONS", Line 23, delete "Pharmacal" and insert -- Pharmacol --, therefor.

On Page 3, in Column 2, item (56) under "OTHER PUBLICATIONS", Line 33, delete "Thermocoecus" and insert -- Thermococcus --, therefor.

On Page 3, in Column 2, item (56) under "OTHER PUBLICATIONS", Line 53, delete "mammal," and insert -- mammary --, therefor.

On Page 4, in Column 1, item (56) under "OTHER PUBLICATIONS", Line 9, delete "1985" and insert -- 1985, --, therefor.

On Page 4, in Column 1, item (56) under "OTHER PUBLICATIONS", Line 18, delete "or" and insert -- of --, therefor.

On Page 4, in Column 1, item (56) under "OTHER PUBLICATIONS", Line 22, delete "3,3`,44`-tetrachlorobiphenyl" and insert -- 3,3`,4,4`-tetrachlorobiphenyl --, therefor.

On Page 4, in Column 2, item (56) under "OTHER PUBLICATIONS", Line 5, delete "Toeopherol" and insert -- Tocopherol --, therefor.

On Page 4, in Column 2, item (56) under "OTHER PUBLICATIONS", Line 21, delete "F" and insert -- E --, therefor.

On Page 4, in Column 2, item (56) under "OTHER PUBLICATIONS", Line 31, delete "Thyrotropim-stimulated" and insert -- Thyrotropin-stimulated --, therefor.

CERTIFICATE OF CORRECTION (continued)
U.S. Pat. No. 10,704,102 B2

On Page 4, in Column 2, item (56) under "OTHER PUBLICATIONS", Line 32, delete "exptession" and insert -- expression --, therefor.

In the Specification

In Column 22, Line 21, delete "C-A," and insert -- CA, --, therefor.

In the Claims

In Column 26, Line 54, in Claim 8, delete "a".